United States Patent
Hanada

(10) Patent No.: US 9,830,687 B2
(45) Date of Patent: Nov. 28, 2017

(54) IMAGE PROCESSING DEVICE, MAGNETIC RESONANCE IMAGING APPARATUS AND IMAGE PROCESSING METHOD

(71) Applicant: HITACHI, LTD., Tokyo (JP)

(72) Inventor: Hikaru Hanada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 163 days.

(21) Appl. No.: 14/770,980

(22) PCT Filed: Feb. 18, 2014

(86) PCT No.: PCT/JP2014/053679
§ 371 (c)(1),
(2) Date: Aug. 27, 2015

(87) PCT Pub. No.: WO2014/132830
PCT Pub. Date: Sep. 4, 2014

(65) Prior Publication Data
US 2016/0012569 A1    Jan. 14, 2016

(30) Foreign Application Priority Data
Feb. 28, 2013    (JP) .................................. 2013-038135

(51) Int. Cl.
| | |
|---|---|
| G06K 9/00 | (2006.01) |
| G06K 9/40 | (2006.01) |
| G06T 5/00 | (2006.01) |
| G06T 3/40 | (2006.01) |
| A61B 5/00 | (2006.01) |
| G06T 5/50 | (2006.01) |

(Continued)

(52) U.S. Cl.
CPC ............ *G06T 5/002* (2013.01); *A61B 5/7246* (2013.01); *G06T 3/4038* (2013.01); *G06T 5/50* (2013.01); *A61B 5/055* (2013.01); *A61B 8/00* (2013.01); *G06T 2207/10088* (2013.01); *G06T 2207/20024* (2013.01); *G06T 2207/20182* (2013.01); *G06T 2207/20221* (2013.01); *G06T 2207/30004* (2013.01)

(58) Field of Classification Search
None
See application file for complete search history.

(56) References Cited

U.S. PATENT DOCUMENTS

| | | | |
|---|---|---|---|
| 2003/0011368 A1* | 1/2003 | Abe | G01R 33/563 324/309 |
| 2004/0066978 A1 | 4/2004 | Nanbu | |

(Continued)

FOREIGN PATENT DOCUMENTS

| | | |
|---|---|---|
| JP | 2003-61964 A | 3/2003 |
| JP | 2003-190148 A | 7/2003 |

(Continued)

*Primary Examiner* — Sean Conner

(57) ABSTRACT

In order to reduce errors in assessment of a structure caused by noise and remove the noise superimposed in an image without causing artificiality in the result image after the removal while retaining significant information, a similarity is calculated by comparing a reference image generated from a plurality of original images with each original image and set as an index of noise determination. The respective original images are smoothed and synthesized using the said index to acquire a final image after the noise removal.

9 Claims, 18 Drawing Sheets

(51) Int. Cl.
*A61B 8/00* (2006.01)
*A61B 5/055* (2006.01)

(56) References Cited

U.S. PATENT DOCUMENTS

| | | | |
|---|---|---|---|
| 2008/0009703 A1 | 1/2008 | Bito et al. | |
| 2010/0171840 A1* | 7/2010 | Yonekura | G06T 5/50 |
| | | | 348/208.4 |
| 2013/0063614 A1* | 3/2013 | Tsutsumi | H04N 5/2258 |
| | | | 348/208.4 |

FOREIGN PATENT DOCUMENTS

| | | |
|---|---|---|
| JP | 2007-301118 A | 11/2007 |
| JP | 2010-181951 A | 8/2010 |
| WO | 02/086821 A1 | 10/2002 |

\* cited by examiner

FIG. 11
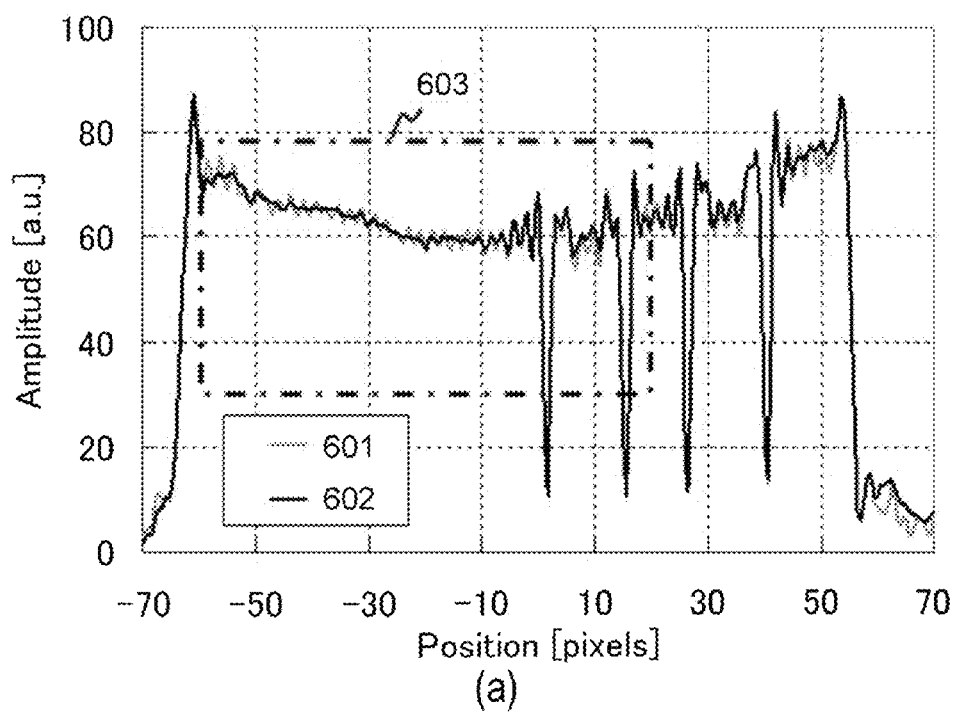
(a)
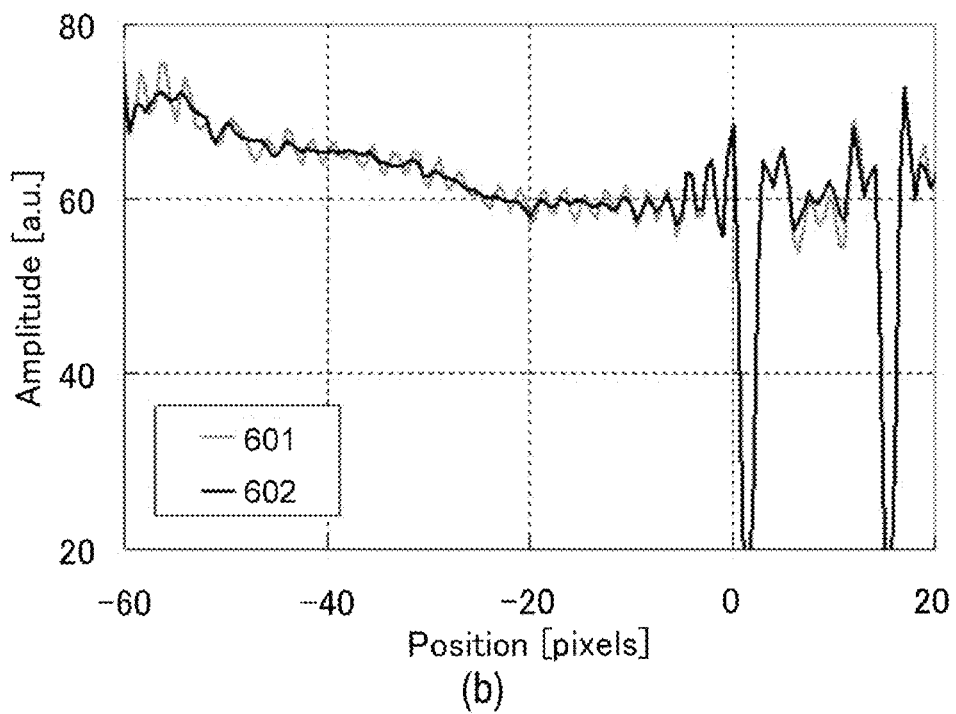
(b)

IMAGE PROCESSING DEVICE, MAGNETIC RESONANCE IMAGING APPARATUS AND IMAGE PROCESSING METHOD

TECHNICAL FIELD

The present invention relates to a magnetic resonance imaging (hereinafter, referred to as MRI) apparatus for measuring a nuclear magnetic resonance signal (hereinafter, referred to as an NMR signal) from hydrogen, phosphorus, or the like in an object and imaging nuclear density distribution, relaxation time distribution, or the like, and particularly to an image filtering technique.

BACKGROUND ART

The MRI apparatus is an apparatus that measures an NMR signal generated by spin of nuclei composing an object, in particular human body tissues, and images forms and the like of the head, abdomen, extremities, etc. two-dimensionally or three-dimensionally. A thermal noise caused by irregular motions of electrons in an electronic circuit is included in the NMR signal measured by the MRI apparatus. Therefore, noises are superimposed in the acquired image, which reduces an SN ratio of the image.

As a method to solve this problem, filtering can be recommended. Because filtering is a post-process to be performed after measurement, there is an advantage that it does not accompany measurement time extension. However, noises as well as required signal information are lost in a linear filter, and this results in a problem such as a blurred image, i.e. resolution reduction.

In order to avoid this, the filtering method that prevents the loss of the required information included in an image is suggested, and there is the following method as an example. The method holds the structure of the image by changing a weighting function shape of the filter based on the result after detecting directionality of a target pixel and the surrounding texture or detecting a structure of an edge or the like (for example, see Non-patent Literature 1). At this time, the detection of the directionality and the structure is performed on the basis of a pixel value of the image.

CITATION LIST

Non-Patent Literature

NPTL 1: H. Takeda et al., Kernel Regression for Image Processing and Reconstruction, IEEE Trans. Img. Process, 2008 vol. 16, no. 2 p 349

NPTL 2: David A. Feinberg et al., Halving MR Imaging Time by Conjugation: Demonstration at 3.5 kG, Radiology, Vol. 161, no. 2, p 527-531, (1986)

SUMMARY OF INVENTION

Technical Problem

However, in the method of detecting the texture directionality and the structure as disclosed in NPTL 1, pixel value fluctuation is assessed as the texture and the structure, and pixel value fluctuation by noise is also saved. Also, because the structure is detected from an image, there is a case where noises are also assessed as the structure. Therefore, an artificial structure can be generated after filtering.

The present invention is made in light of the above circumstances and has a purpose to provide a technique for reducing errors in assessment of a structure caused by noise and removing noises superimposed in an image without causing artificiality in a result image after the removal while retaining significant information.

Solution to Problem

The present invention calculates a similarity by comparing a reference image generated from a plurality of original images with each original image and sets the similarity as an index of noise determination. The respective original images are smoothed and synthesized using the said index to acquire a final image after the noise removal. At this time, the original image may be divided for each of a plurality of wavelength bands based on the maximum wavelength of a noise to generate and smooth the above reference image.

Advantageous Effects of Invention

Errors in assessment of a structure caused by noise are reduced, and noises superimposed in an image can be removed without causing artificiality in a result image after the removal while retaining significant information.

BRIEF DESCRIPTION OF DRAWINGS

FIG. 11(a) is a profile graph of an image in which a result of the filtering process of the first embodiment is compared with a result of simple addition, and FIG. 11(b) is a magnified diagram of a part of FIG. 11(a).

DESCRIPTION OF EMBODIMENTS

First Embodiment

Hereinafter, a desirable embodiment related to the present invention will be described in detail according to the attached diagrams. Additionally, in all the diagrams for explaining the embodiments of the invention, the same symbols are used for the same functions, and the repeated explanations are omitted unless clearly indicated otherwise.

The present embodiment describes a case where an MRI apparatus is used as an image acquisition device as an example.

Figure 1:
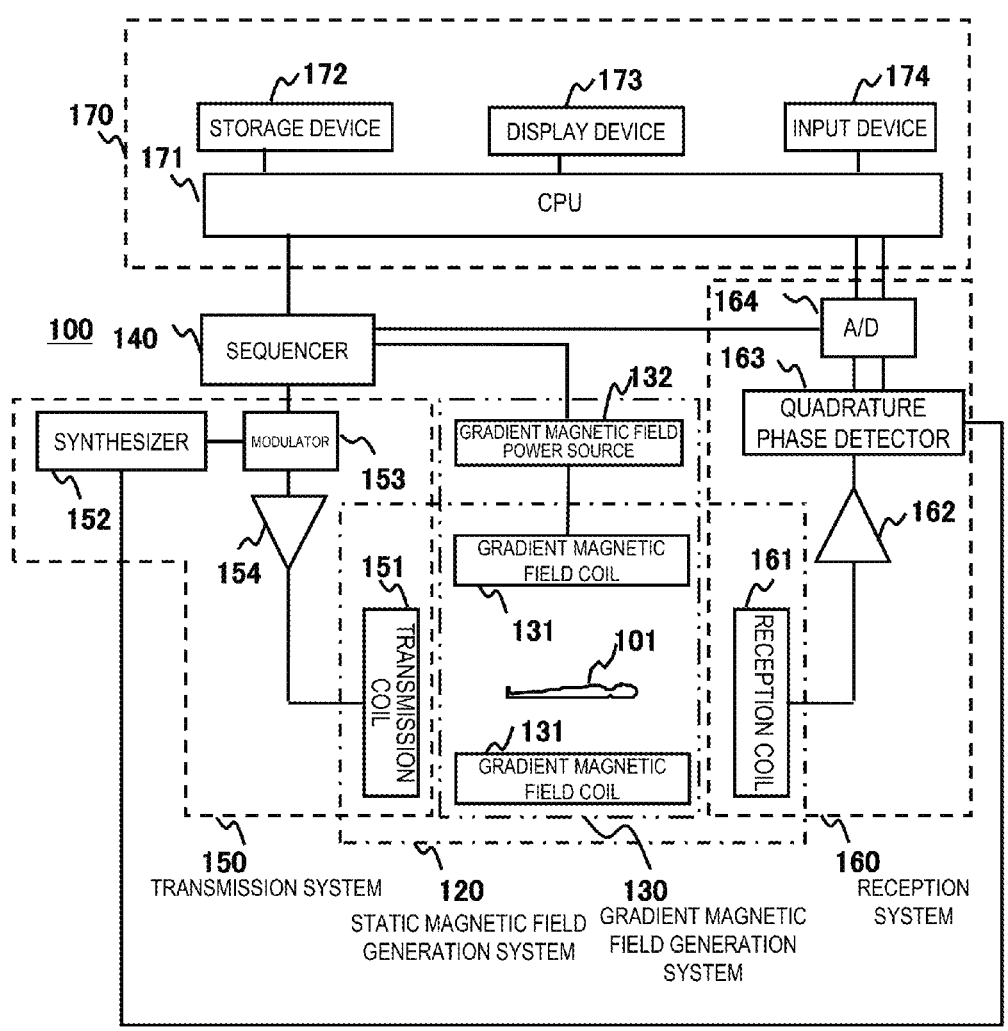
FIG. 1 is an overall configuration diagram of the MRI apparatus of the first embodiment.

First, an example of the overview of the MRI apparatus in the present embodiment will be described based on FIG. 1. FIG. 1 is a block diagram showing an overall configuration of the MRI apparatus in the first embodiment.

The MRI apparatus 100 of the present embodiment acquires tomographic images of an object using the NMR phenomenon and comprises the static magnetic field generation system 120, the gradient magnetic field generation system 130, the high-frequency magnetic field generation system (hereinafter, referred to as the transmission system) 150, the high-frequency magnetic field detection system (hereinafter, referred to as the reception system) 160, the control processing system 170, and the sequencer 140 as shown in FIG. 1.

The static magnetic field generation system 120 generates a homogeneous static magnetic field in a direction orthogonal to the body axis in a space surrounding the object 101 in case of a vertical magnetic field type and in the body-axis direction in case of a horizontal magnetic field type and includes a static magnetic field generating source of a permanent magnet type, a normal conducting type, or a superconducting type, which is to be disposed around the object 101.

The gradient magnetic field generation system 130 comprises the gradient magnetic field coils 131 wound in the three directions X, Y, and Z that are coordinate systems (device coordinate systems) of the MRI apparatus 100 as well as the gradient magnetic field power source 132 driving the respective gradient magnetic field coils and applies the gradient magnetic fields Gx, Gy, and Gz in the three directions X, Y, and Z by driving the gradient magnetic field power source 132 of the respective gradient magnetic field coils 131 according to the command from the sequencer 140 to be described later.

The transmission system 150 irradiates a high-frequency magnetic field pulse (hereinafter, referred to as "RF pulse") to the object 101 in order to induce nuclear magnetic resonance to nuclear spins of atoms composing biological tissues of the object 101 and comprises the high-frequency oscillator (synthesizer) 152, the modulator 153, the high-frequency amplifier 154, and the high-frequency coil (transmission coil) 151 on the transmission side. The high-frequency oscillator 152 generates and outputs an RF pulse at a timing commanded from the sequencer 140. The modulator 153 performs amplitude modulation for the output RF pulse, and the high-frequency amplifier 154 amplifies the RF pulse for which amplitude modulation was performed and supplies the RF pulse to the transmission coil 151 disposed in the vicinity of the object 101. The transmission coil 151 irradiates the supplied RF pulse to the object 101.

The reception system 160 detects a nuclear magnetic resonance signal (an echo signal or an NMR signal) emitted by nuclear magnetic resonance of nuclear spins of atoms composing biological tissues of the object 101 and comprises the high-frequency coil (reception coil) 161 on the reception side, the signal amplifier 162, the quadrature phase detector 163, and the A/D converter 164. The reception coil 161 is disposed in the vicinity of the object 101 and detects a response NMR signal of the object 101 induced by an electromagnetic wave irradiated from the transmission coil 151. After being amplified by the signal amplifier 162, the detected NMR signal is divided into signals of two orthogonal systems by the quadrature phase detector 163 at a timing commanded from the sequencer 140 and is respectively converted into digital amounts by the A/D converter 164 before being sent to the control processing system 170.

The sequencer 140 applies an RF pulse and a gradient magnetic field pulse according to the instruction from the control processing system 170. Specifically, according to the instruction from the control processing system 170, various commands required for data collection of a tomographic image of the object 101 are transmitted to the transmission system 150, the gradient magnetic field generation system 130, and the reception system 160.

The control processing system 170 controls all of the MRI apparatus 100, calculates various data processes etc., displays as well as saves the process results, and comprises the CPU 171, the storage device 172, the display device 173, and the input device 174. The storage device 172 comprises an internal storage device such as a hard disk and an external storage device such as such as an external hard disk, an optical disk, and a magnetic disk. The display device 173 is a display device such as a CRT display and a liquid crystal display. The input device 174 is an interface for inputting various control information of the MRI apparatus 100 and control information to be processed in the control processing system 170 and comprises, for example, a trackball or a mouse and a keyboard. The input device 174 is disposed in the vicinity of the display device 173. An operator inputs commands and data required for various processes of the MRI apparatus 100 interactively through the input device 174 while watching the display device 173.

The CPU 171 executes a program previously retained in the storage device 172 according to the instruction input by an operator to achieve the respective processes of the control processing system 170 such as controlling operations of the MRI apparatus 100 and processing various data. For example, when data from the reception system 160 is input to the control processing system 170, the CPU 171 executes signal processing, image reconstruction processing, or the like and displays the consequent tomographic image of the object 101 on the display device 173 as well as stores the tomographic image in the storage device 172.

The transmission coil 151 and the gradient magnetic field coils 131 are placed opposite to the object 101 in case of a vertical magnetic field type and placed so that they surround the object 101 in case of a horizontal magnetic field type in a static magnetic field space of the static magnetic field generation system 120 where the object 101 is inserted. Also, the reception coil 161 is placed so that it is opposite to or surrounds the object 101.

Currently, an imaging target nuclide of MRI apparatuses is a hydrogen nucleus (proton) which is clinically prevalent and is the main component of the object 101. By imaging information in relation to spatial distribution of proton density or spatial distribution of relaxation time in an exited state in the MRI apparatus 100, forms or functions of body parts such as the head, abdomen, extremities, etc. are imaged two-dimensionally or three-dimensionally.

Figure 2:
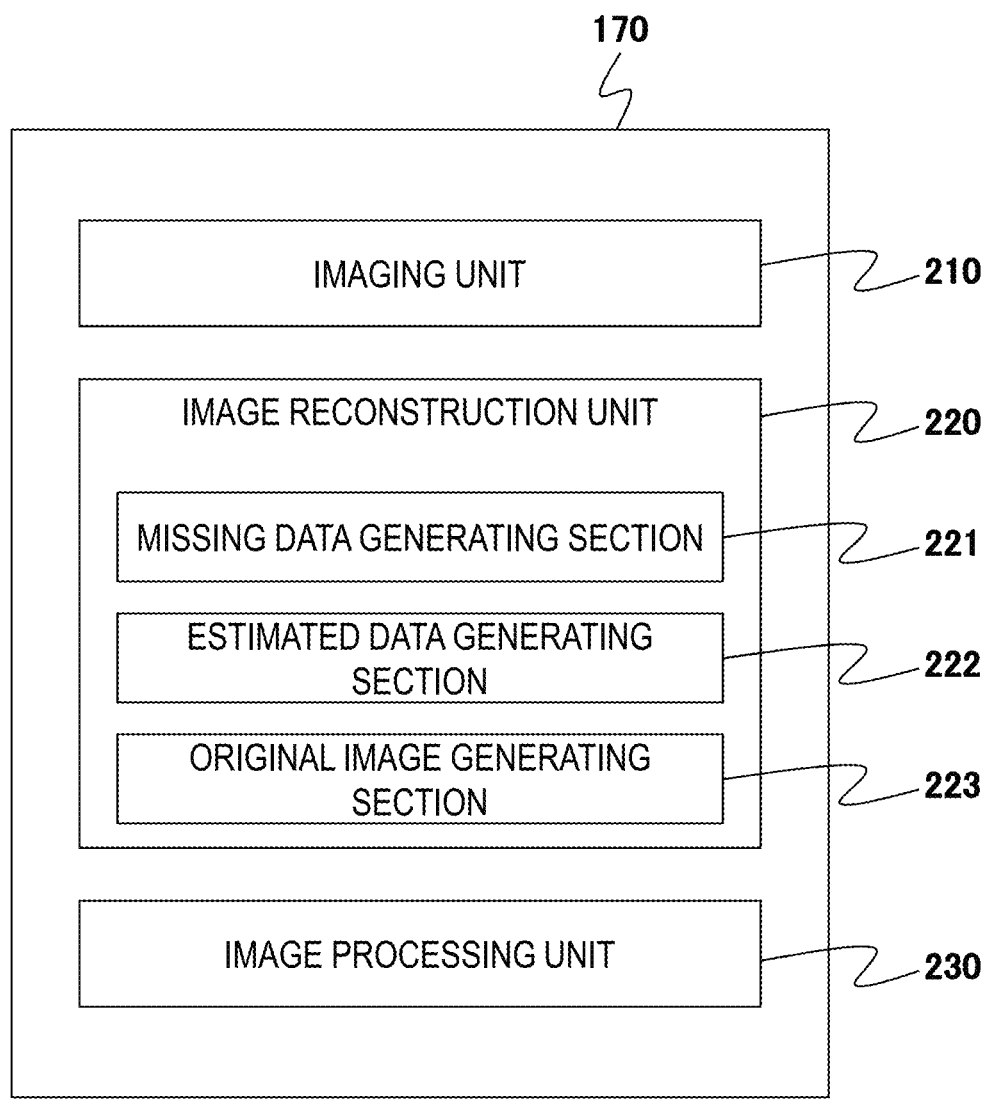
FIG. 2 is a functional block diagram of the control processing system of the MRI apparatus of the first embodiment.

The control processing system 170 of the present embodiment controls operations of the measurement system comprising the static magnetic field generation system 120, the gradient magnetic field generation system 130, the high-frequency magnetic field generation system 150, and the high-frequency magnetic field detection system 160 according to the pulse sequence as shown in FIG. 2, disposes the measured nuclear magnetic resonance signal in a k-space, and then achieves functions of the imaging unit 210 acquiring Raw data, the image reconstruction unit 220 reconstructing an image from the Raw data, and the image processing unit (image processing device) 230 performing image processing for the image.

The image processing unit 230 of the present embodiment performs a filtering process to reduce noise using a plurality of images in which the same imaging range is imaged. The plurality of images used for the filtering process by the image processing unit 230 are referred to as "a plurality of original images" or "an original image group", and in case of indicating an image from among the original image group, the image is simply referred to as "an original image". Also, an image after the filtering process is referred to as "a synthesized image".

Specifically, the image processing unit 230 of the present embodiment generates a reference image by synthesizing a plurality of original images, calculates a similarity by comparing the generated reference image with each of the plurality of original images, smoothes the original images based on the calculated similarity, and then synthesizes the plurality of the smoothed original images to acquire a synthesized image.

Additionally, an original image group is acquired by the image reconstruction unit 220 reconstructing images from a Raw data group acquired by the imaging unit 210. The imaging unit 210 acquires the Raw data group by measurement using a plurality of the reception coils 161, for example. Also, the Raw data group may be acquired by performing the measurement multiple times under the same imaging conditions. A plurality of images in which the same imaging range is imaged are used as original images in order to improve a noise extraction accuracy by using images in which different random noises are superimposed.

Figure 3:
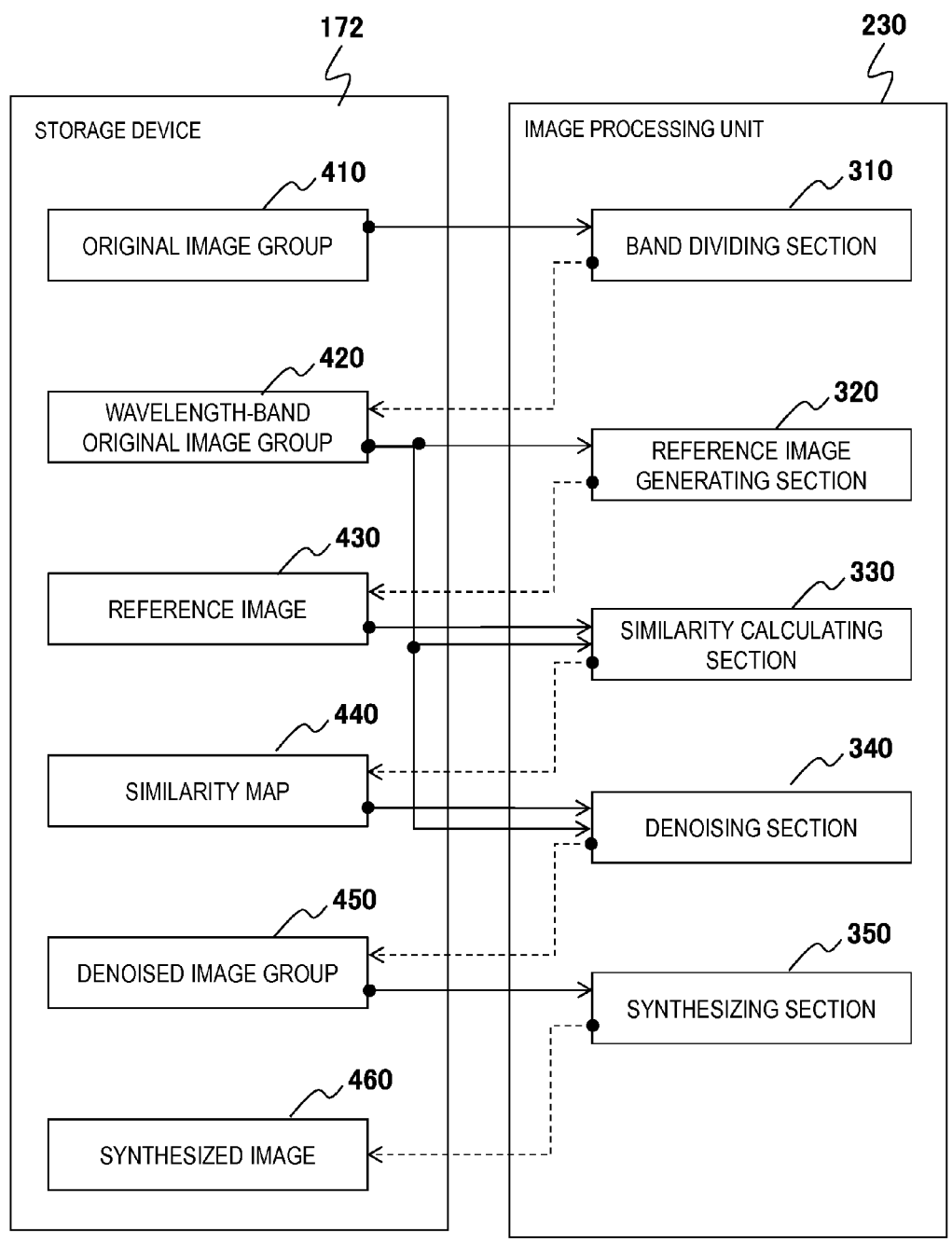
FIG. 3 is a diagram for explaining the functional blocks of the image processing unit of the first embodiment and data to be generated by each function.

In order to achieve the above filtering process, as shown in FIG. 3, the image processing unit 230 of the present embodiment comprises the band dividing section 310 for dividing a plurality of the original images 410 (original image group) in each predetermined wavelength band and generating a plurality of the wavelength-band original images 420 (wavelength-band original image group), the reference image generating section 320 for synthesizing the plurality of the wavelength-band original images 420 in each wavelength band to generate the reference images 430 in each wavelength band, the similarity calculating section 330 for comparing the plurality of the wavelength-band original images 420 with the reference images 430 in the same band respectively and calculating a similarity for the respective wavelength-band original images 420 to generate the similarity map 440, the denoising section 340 for generating the denoised images 450 (a plurality of denoised images; a denoised image group) respectively from the wavelength-band original images 420 by smoothing the plurality of the wavelength-band original images 420 using the respective similarities of the said wavelength-band original images 420, and the synthesizing section 350 for synthesizing a plurality of the denoised images 450 to generate the synthesized image 460.

Data and an image group to be generated during processes executed by each section are stored in a RAM, for example, of the storage device 172 respectively.

Figure 4:
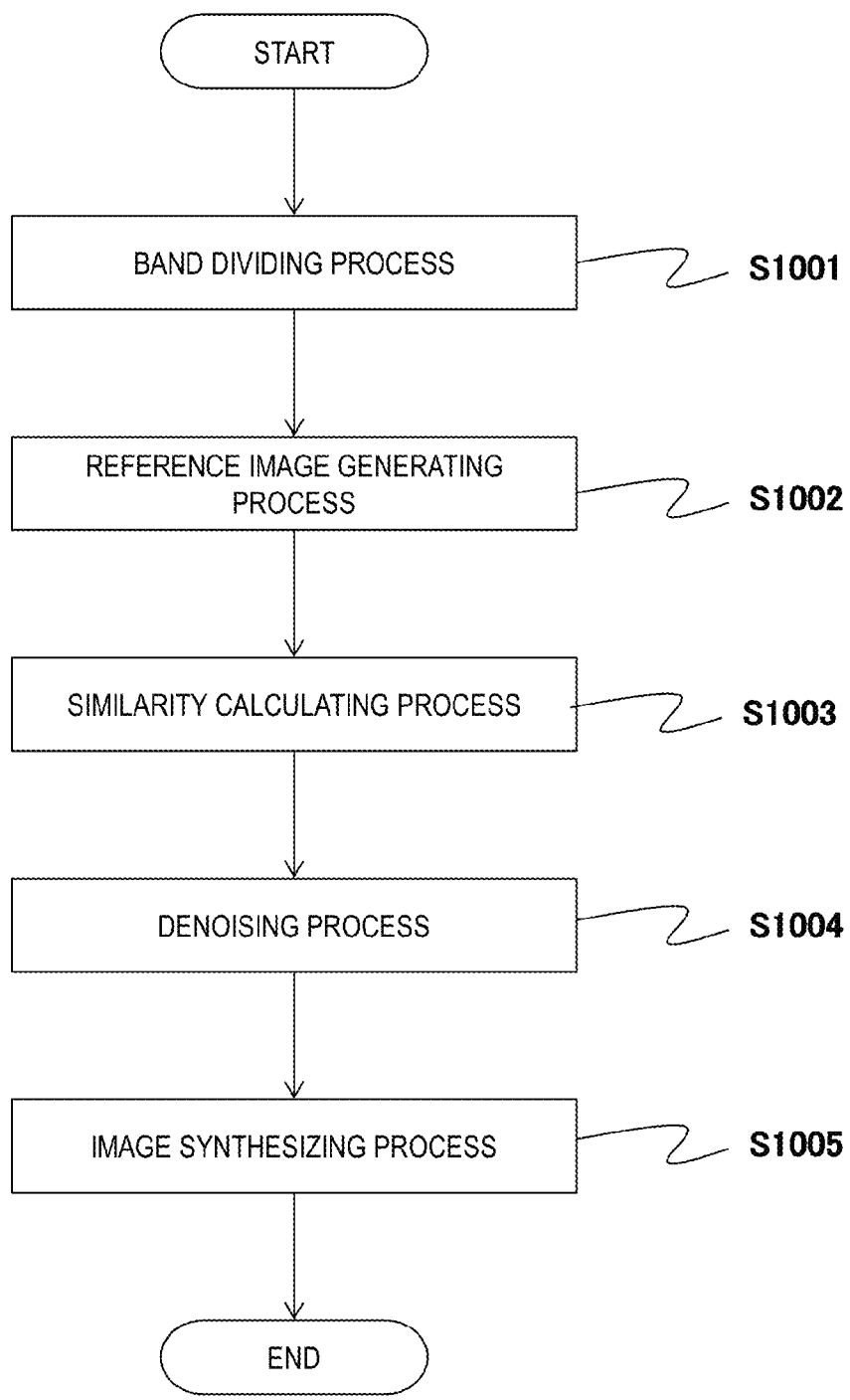
FIG. 4 is a flow chart of the filtering process of the first embodiment.

The flow of the above filtering process of the present embodiment will be described. FIG. 4 is a process flow for explaining the filtering process of the present embodiment. Here, the number of the original images 410 is N, and the band dividing section 310 divides the respective original images 410 into M wavelength bands.

N and M are integers equal to or more than 1.

First, the band dividing section 310 performs a band dividing process for each of the N original images 410 (Step S1001). Hence, the N×M wavelength-band original images 420 are acquired.

Next, the reference image generating section 320 performs a reference image generating process to acquire the reference images 430 in the respective wavelength bands (Step S1002). The reference image 430 is generated in each band. Therefore, the M reference images 430 are acquired here.

Next, the similarity calculating section 330 performs a similarity calculating process to calculate a similarity (Step S1003). In the present embodiment, similarities in the two directions X and Y are calculated for each pixel in the N×M wavelength-band original images 420 respectively to generate the similarity maps 440. Therefore, the 2×N×M similarity maps 440 are acquired.

Then, the denoising section 340 performs a denoising process to generate the denoised images 450 (Step S1004). In the present embodiment, the denoising process in the two directions X and Y are performed for each pixel in the N×M wavelength-band original images 420 respectively. Therefore, N×M denoised images are acquired.

Finally, the synthesizing section 350 performs an image synthesizing process to acquire the synthesized image 460 (Step S1005). Here, the N×M denoised images after the denoising process are synthesized to generate one sheet of the synthesized image 460.

Hereinafter, each process will be described in detail.

<Band Dividing Process>

The band dividing section 310 performs a band dividing process dividing the original image group 410 in each predetermined wavelength band as described above. In the present embodiment, a case where the filters divide the image group into an image group having a larger band than a predetermined cut-off wavelength and an image group having a band equal to or less than the cut-off wavelength will be described as an example. The band dividing section of the present embodiment achieves this using a low-pass filter and a high-pass filter for which the same cut-off wavelength is set. Additionally, wavelength bands to be divided are not limited to two.

Figure 5:
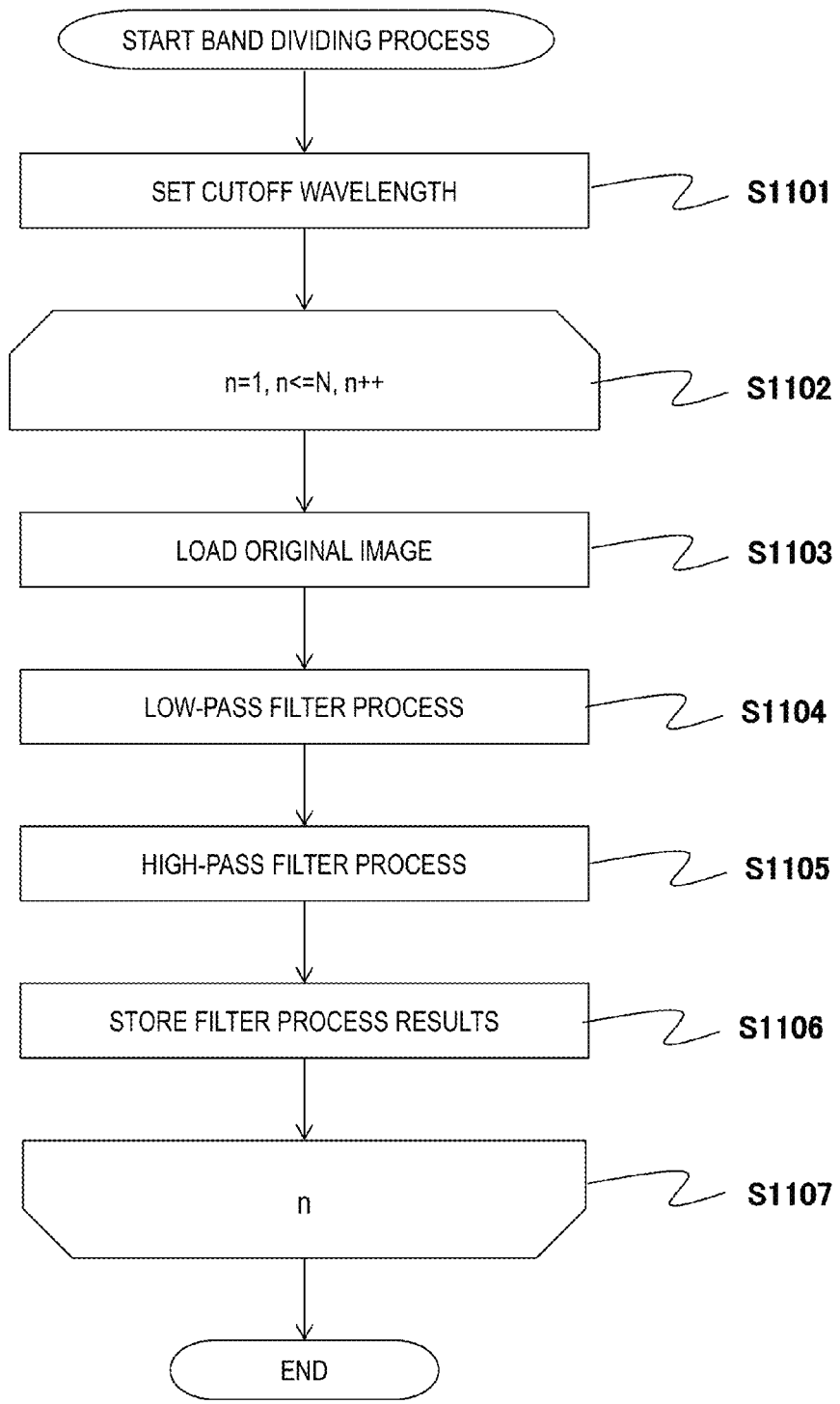
FIG. 5 is a flow chart of the band dividing process of the first embodiment.

FIG. 5 is a process flow of the band dividing process of the present embodiment. Additionally, it is assumed that original image numbers are previously provided for the respective original images 410. Here, an original image of the original image number n is expressed as $I_{Org}(n, x, y)$.

The band dividing section 310 sets a cut-off wavelength of a low-pass filter and a high-pass filter (Step S1101).

Then, processes in the following Steps S1103 to S1104 are executed for a plurality of original images (original image group: $I_{Org}(n, x, y)$) respectively while increasing the original image number n in increments of 1 from 1 (Steps S1102 and S1107).

The band dividing section 310 loads the n-th original image ($I_{Org}$(n, x, y)) (Step S1103). Then, a low-pass filtering process by a low-pass filter is performed for an original image group $I_{Org}$(n, x, y) (Step S1104). Also, a high-pass filtering process by a high-pass filter is performed for the original image group (Step S1105). Either of both the filtering processes may be performed first.

Then, the band dividing section 310 stores the obtained low-pass filter result and high-pass filter result respectively as the wavelength-band original images 420 in the storage device 172 (Step S1106). At this time, band numbers are provided for each band after wavelength band division. A wavelength-band original image of the band number m is expressed as $I_{Sep}$(m, n, x, y). In the present embodiment, the band number 1 is provided for the low-pass filter result, and it is referred to as a first wavelength-band original image $I_{Sep}$(1, n, x, y). Also, the band number 2 is provided for the high-pass filter result, and it is referred to as a second wavelength-band original image $I_{Sep}$(2, n, x, y).

Here, the details of setting the cut-off wavelength in Step S1101 are described. The cut-off wavelength to be set is determined according to the wavelength of a noise. That is, when the maximum noise wavelength $\lambda_{Noise}$ is set to J(pixels), the cut-off wavelength becomes 1/J(1/pixels). For example, when the maximum noise wavelength $\lambda_{Noise}$ is set to 3 pixels, the cut-off wavelength becomes ⅓(1/pixels). Although an appropriate maximum noise wavelength $\lambda_{Noise}$ is 3 pixels generally, the point (cut-off wavelength [pixels]) is increased in proportion to an interpolation magnification in case of using an interpolated image as an original image.

Additionally, a Gaussian filter may be used as a low-pass filter. A filter having gradual cutoff characteristics such as a Gaussian filter is more desirable than that having steep cutoff characteristics because ringing hardly appears in an image. In this case, the cut-off wavelength $\lambda_{Cutoff}$ is set as follows.

The amplitude transmission characteristics $H(\lambda)$ of a Gaussian filter is expressed in the following formula (1).

[Formula 1]

$$H(\lambda) = \exp\left[-\pi\left(\frac{\alpha \lambda_{Cutoff}}{\lambda}\right)^2\right] \quad (1)$$

Additionally, α is expressed in the following formula (2).

[Formula 2]

$$\alpha = \sqrt{\frac{\ln 2}{\pi}} \quad (2)$$

Here, λ is a wavelength (pixels). When an attenuation factor (%) of signal components equal to or less than the maximum noise wavelength $\lambda_{Noise}$ is set as δ from Formulas 1 and 2, the cut-off wavelength $\lambda_{Cutoff}$ can be calculated by the following formula (3).

[Formula 3]

$$\lambda_{Cutoff} = \frac{\lambda_{Noise}}{\alpha}\left(-\frac{\ln(1-\delta/100)}{\pi}\right)^{1/2} \quad (3)$$

In this case, for example, when the maximum noise wavelength $\lambda_{Noise}$ is set to 3 (pixels) and the attenuation factor δ is set to 99(%) as described above, the cut-off wavelength $\lambda_{Cutoff}$ becomes approximately 7.7 (pixels).

Also, when a Gaussian filter is used as a low-pass filter, the low-pass filtering process in the above Step S1104 follows the formula (4) below.

[Formula 4]

$$I_{Sep}(1,n,x,y) = I_{Org}(n,x,y) * h(\tau) \quad (4)$$

Here, h(τ) is a weighting function of a Gaussian filter.

Also, the high-pass filtering process in Step S1105 follows the formula (5) below.

[Formula 5]

$$I_{Sep}(2,n,x,y) = I_{Org}(n,x,y) - I_{Sep}(1,n,x,y) \quad (5)$$

Additionally, the maximum noise wavelength $\lambda_{Noise}$ is set by a user through the GUI to be described later. Also, the maximum noise wavelength $\lambda_{Noise}$ may be set in the storage device 172 in advance.

<Reference Image Generating Process>

Figure 6:
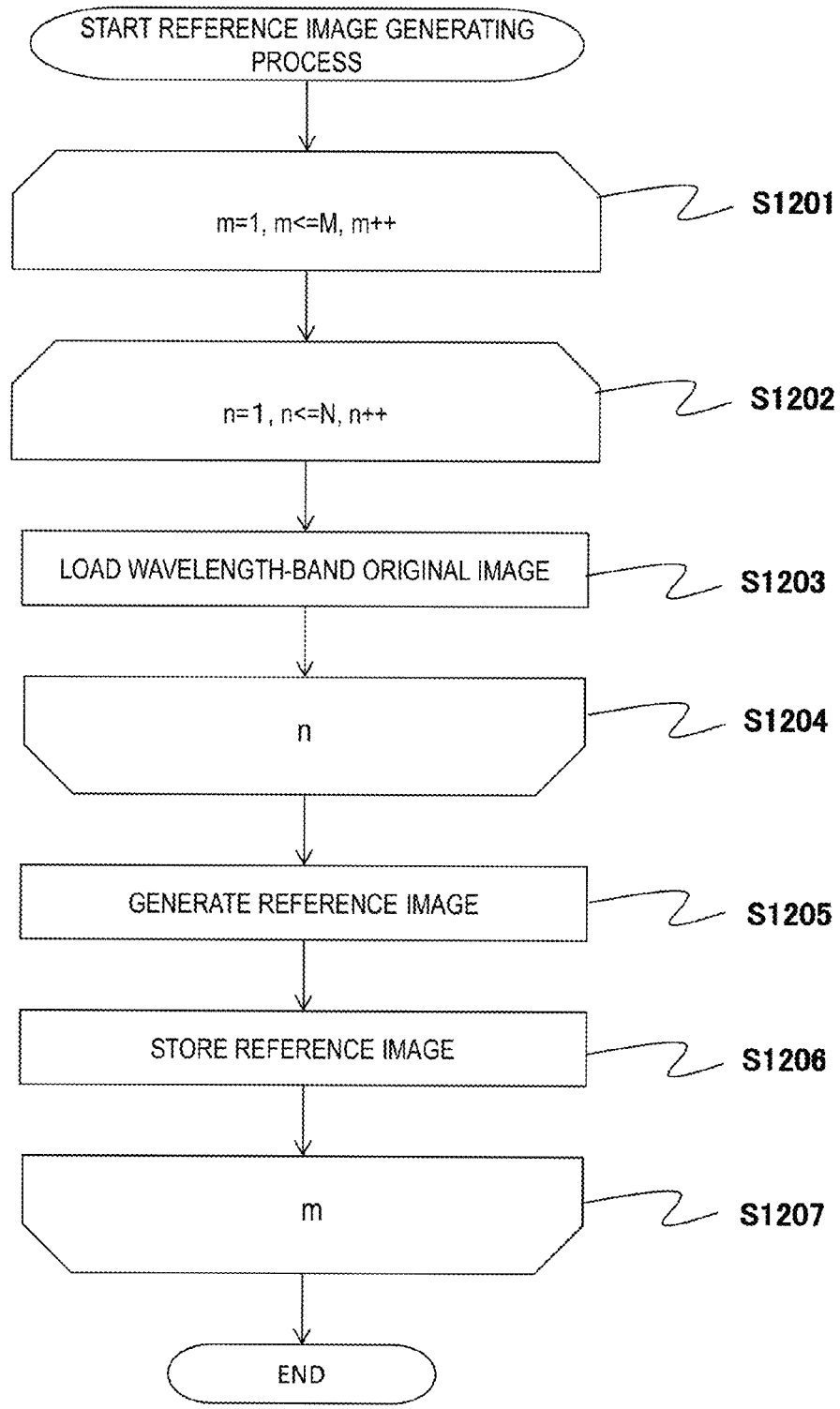
FIG. 6 is a flow chart of the reference image generating process of the first embodiment.

Next, the details of the reference image generating process by the reference image generating section 320 will be described. In the reference image generating process, a reference image considered to be correct provisionally is generated in each wavelength band. In the present embodiment, the reference image 430 is generated using the wavelength-band original images 420 in each wavelength band that were generated from the respective original images 410. FIG. 6 is a flow of the reference image generating process of the present embodiment.

The reference image generating section 320 repeats the following processes from Steps S1202 to S1206 by the number M (M is an integer equal to or more than 2) of the divided wavelength bands (Steps S1201 and S1207). In the present embodiment, the processes are repeated twice because the wavelength band is divided into two by a low-pass filter and a high-pass filter using a cut-off wavelength. In case of m=1, the first wavelength-band original image $I_{Sep}$(1, n, x, y) that is a low-pass filter result is processed, and in case of m=2, m=1, the second wavelength-band original image $I_{Sep}$(2, n, x, y) that is a high-pass filter result is processed.

The reference image generating section 320 loads all of the wavelength-band original images 420 of the band number m that were generated from the n sheets of the original images 410 (Step S1202, S1203, and S1204).

Then, the reference image generating section 320 synthesizes the loaded wavelength-band original images 420 to acquire one of the reference images 430 in each wavelength band (Step S1205). This synthesizing process, for example, follows the formula (6) below to calculate an average value of the wavelength-band original images 420 in the same wavelength band that were acquired from all the original images 410.

[Formula 6]

$$I_{Ref}(m, x, y) = \frac{1}{N}\sum_{n=0}^{N} I_{Sep}(m, n, x, y) \quad (6)$$

Here, $I_{Ref}$(m, x, y) is the reference image 430 of the band number m, N is the total number of the original images 410, which is the number of wavelength-band original images of the band number m that were acquired from the N sheets of the original images 410.

The reference image generating section 320 stores the acquired reference image $I_{Ref}(m, x, y)$ 430 in the storage device 172 (Step S1206).

Hereinafter, in the present embodiment, a reference image IRef(1, x, y) acquired from the first wavelength-band original image ISep(1, n, x, y) group is referred to as a first reference image, and a reference image IRef(2, x, y) acquired from the second wavelength-band original image ISep(2, n, x, y) group is referred to as a second reference image.

Additionally, although a reference image is acquired in each wavelength band by calculating an average value in the present embodiment, the calculation method is not limited to this. For example, a square root of a square sum of each wavelength-band original image is calculated to acquire a reference image.

<Similarity Calculating Process>

Figure 7:
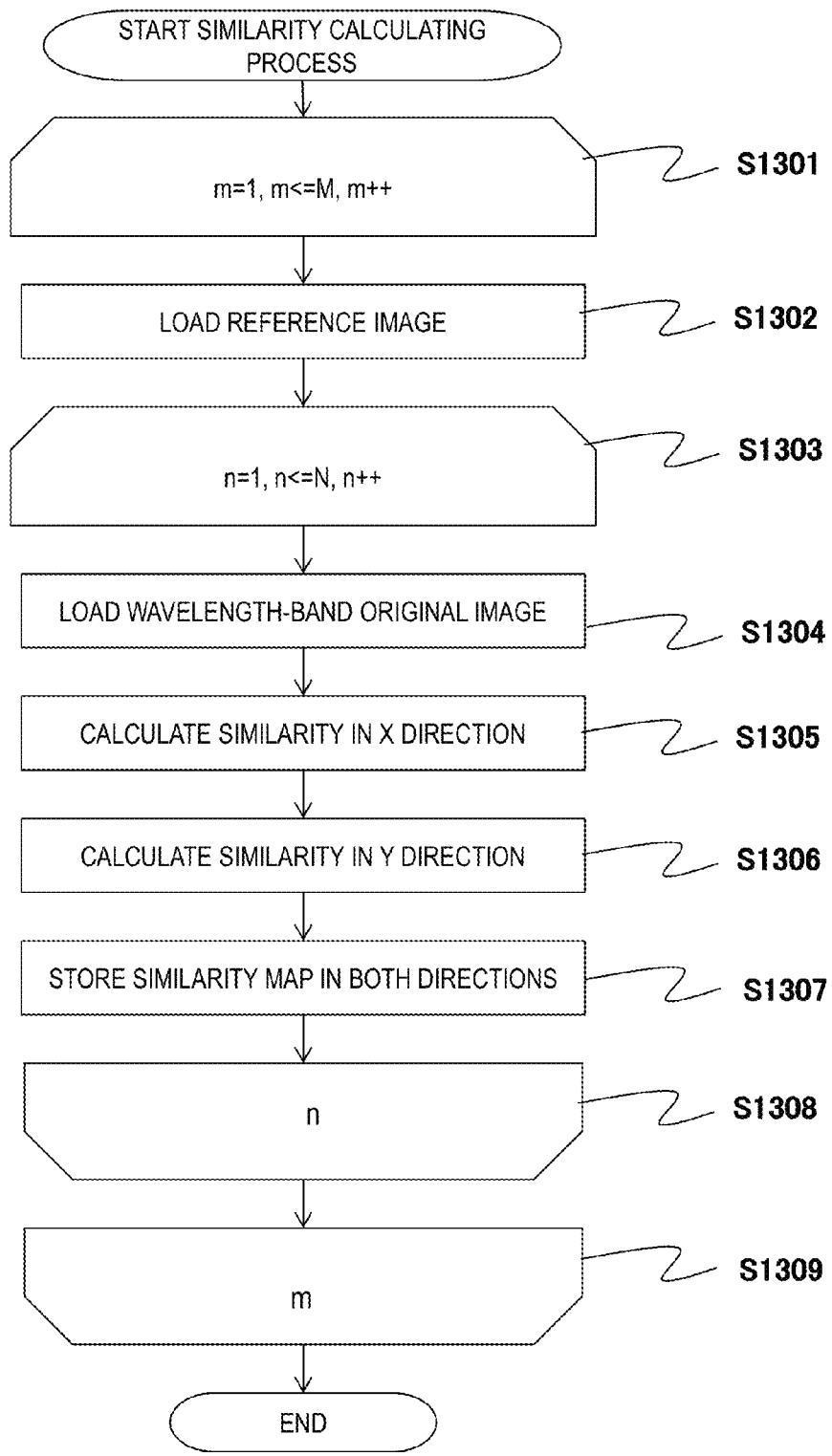
FIG. 7 is a flow chart of the similarity calculating process of the first embodiment.

Next, a similarity calculating process by the similarity calculating section 330 will be described. In the similarity calculating process, a similarity to the reference image 430 is calculated for the respective wavelength-band original images 420. The similarity calculation is performed for each pixel in the x and y directions. FIG. 7 is a flow of the similarity calculating process of the present embodiment.

The similarity calculating section 330 repeats the processes from Steps S1302 to S1309 by the number of divided wavelength bands (Steps S1301 and S1309). In the present embodiment, the processes are repeated twice similarly to the image generating process.

First, the similarity calculating section 330 loads the m-th reference image 430 (Step S1302). In the present embodiment, the first reference image $I_{Ref}(1, x, y)$ is loaded in case of m=1, and the second reference image $I_{Ref}(2, x, y)$ is loaded in case of m=2.

The similarity calculating section 330 executes the processes from Steps S1304 to S1307 for the wavelength-band original images 420 of the band number m that were respectively acquired from the N sheets of the original images 410 (Steps S1303 and S1308).

The similarity calculating section 330 first loads wavelength-band original image $I_{Sep}(m, n, x, y)$ that is the wavelength-band original image 420 of the band number m and generated from the n-th original image 410 (Step S1304).

Next, the similarity calculating section 330 calculates a local similarity between the loaded wavelength-band original image $I_{Sep}(m, n, x, y)$ and the reference image $I_{Ref}(m, x, y)$. Here, a similarity in the x direction is first calculated for each pixel of the wavelength-band original image $I_{Sep}(m, n, x, y)$ to generate a similarity map (x-direction similarity map) (Step S1305). A correlation function is used for a similarity of each pixel, for example. A similarity in the x direction for each pixel (an x-direction similarity map: Similarity X(m, n, x, y)) is calculated according to the following formula (7), for example.

[Formula 7]

$$SimilarityX(m, n, x, y) = \frac{\sum_{i=-L}^{L}\left\{\left(I_{Ref}(m, x+i, y) - \frac{1}{2L}\sum_{i=-L}^{L}I_{Ref}(m, x+i, y)\right)\left(I_{Sep}(m, n, x+i, y) - \frac{1}{2L}\sum_{i=-L}^{L}I_{Sep}(m, n, x+i, y)\right)\right\}}{\sqrt{\sum_{i=-L}^{L}\left(I_{Ref}(m, x+i, y) - \frac{1}{2L}\sum_{i=-L}^{L}I_{Ref}(m, x+i, y)\right)^2}\sqrt{\sum_{i=-L}^{L}\left(I_{Sep}(m, n, x+i, y) - \frac{1}{2L}\sum_{i=-L}^{L}I_{Sep}(m, n, x+i, y)\right)^2}} \quad (7)$$

Here, L is a correlation coefficient calculation range. The correlation coefficient calculation range L is set to the same value as the maximum noise wavelength defined previously, for example. The calculation for a correlation coefficient using the above formula is intended to express a similarity. Additionally, because a similarity is calculated as a correlation coefficient in the present embodiment, the maximum value of similarity is 1, and the minimum value is −1.

Next, the similarity calculating section 330 calculates a similarity in the y direction for each pixel of the wavelength-band original image $I_{Sep}(m, n, x, y)$ to generate a y-direction similarity map: Similarity Y(m, n, x, y) (Step S1306). The y-direction similarity map Similarity Y(m, n, x, y) is calculated according to the following formula (8), for example.

[Formula 8]

$$SimilarityY(m, n, x, y) = \frac{\sum_{i=-L}^{L}\left\{\left(I_{Ref}(m, x, y+i) - \frac{1}{2L}\sum_{i=-L}^{L}I_{Ref}(m, x, y+i)\right)\left(I_{Sep}(m, n, x, y+i) - \frac{1}{2L}\sum_{i=-L}^{L}I_{Sep}(m, n, x, y+i)\right)\right\}}{\sqrt{\sum_{i=-L}^{L}\left(I_{Ref}(m, x, y+i) - \frac{1}{2L}\sum_{i=-L}^{L}I_{Ref}(m, x, y+i)\right)^2}\sqrt{\sum_{i=-L}^{L}\left(I_{Sep}(m, x, y+i) - \frac{1}{2L}\sum_{i=-L}^{L}I_{Sep}(m, x, y+i)\right)^2}} \quad (8)$$

Then, the similarity calculating section 330 stores the similarity map Similarity X(m, n, x, y) in the x direction and the similarity map Similarity Y(m, n, x, y) in the y direction obtained as similarities in the x and y directions of each pixel in the storage device 172 (Step S1307). Additionally, if there is no need to distinguish the x and y directions particularly, the map is referred to as a similarity map Similarity(m, n, x, y).

Additionally, in a case where much noise influence can be found in a calculated similarity, a filter process such as a median filter may be performed for a similarity map. The filter process is performed under the assumption that a similarity changes spatially and continuously.

<Denoising Process>

Next, a denoising process by the denoising section 340 will be described. In the denoising process, noises are removed for each pixel of the original images 410 divided in each wavelength band, i.e. the wavelength-band original images 420. The noise removal is performed for each pixel using a weighting function generated according to the similarity of the said pixel. The weighting function has a steeper shape as a similarity of the pixel is higher. This is because it is difficult to smooth a pixel as the similarity is higher and it is easy to smooth a pixel as the similarity is low.

Figure 8:
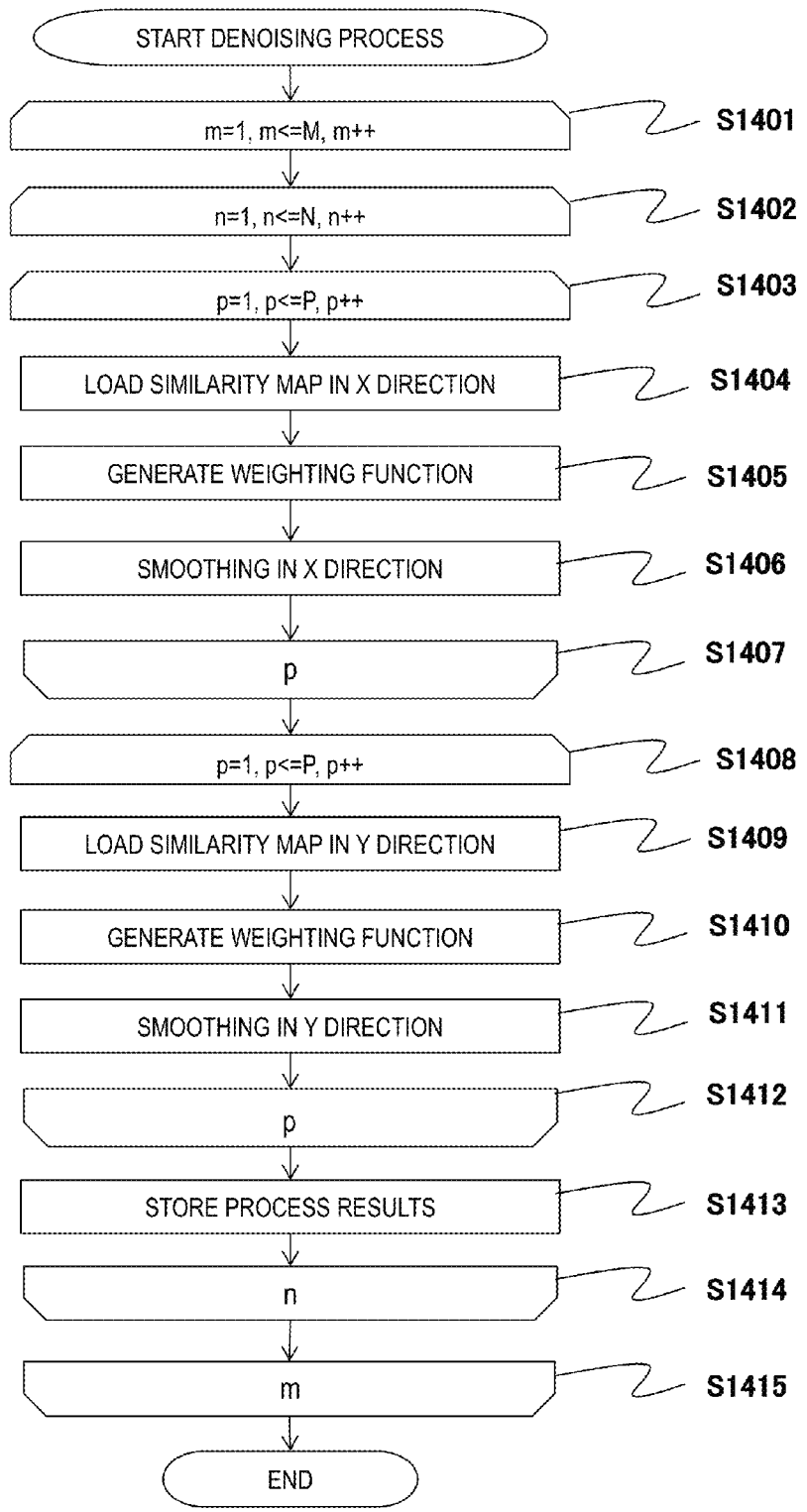
FIG. 8 is a flow chart of the denoising process of the first embodiment.

FIG. 8 is a flow of the denoising process of the present embodiment. In the present embodiment, weighting functions are generated respectively in the x and y directions for each pixel of the respective wavelength-band original images 420 to perform a filtering process. Here, the pixel number p is provided for each pixel (x, y).

The number of all the pixels is P (P is an integer equal to or more than 1).

The denoising section 340 repeats the processes from Steps S1402 to S1414 in each divided wavelength band (Steps S1402 and S1415). In the present embodiment, the processes are repeated twice similarly to the reference image generating process.

Also, the denoising section 340 repeats the processes from Steps S1403 to S1413 for the respective wavelength-band original image groups 420 in the same wavelength band (Steps S1402 and S1414). Here, the processes are repeated N times.

Also, the denoising section 340 performs the processes from Steps S1404 to S1406 for all the pixels in order (Steps S1403 and S1407). Here, the processes are repeated P times.

The denoising section 340 loads the similarity map Similarity X(m, n, x, y) in the x direction of the pixel p=(x, y) (Step S1404). Then, a weighting function of the pixel p is generated using the loaded similarity map Similarity X(m, n, x, y) (Step S1405). The weighting function is generated according to the following formula (9) using the similarity map Similarity(m, n, x, y) and the cut-off wavelength $\lambda_{Cutoff}$, for example.

[Formula 9]

$$h_{Denoise}(\tau) = \begin{cases} \frac{1}{\alpha \cdot \lambda_{Cutoff}} \exp\left\{-\pi\left(\frac{\tau}{\alpha \cdot \lambda_{Cutoff} \cdot (1 - Similarity(m, n, x, y))}\right)\right\} & \text{if}(Similarity(m, n, x, y) > 0) \\ \frac{1}{\alpha \cdot \lambda_{Cutoff}} \exp\left\{-\pi\left(\frac{\tau}{\alpha \cdot \lambda_{Cutoff}}\right)\right\} & \text{else} \end{cases}$$

Figure 9:
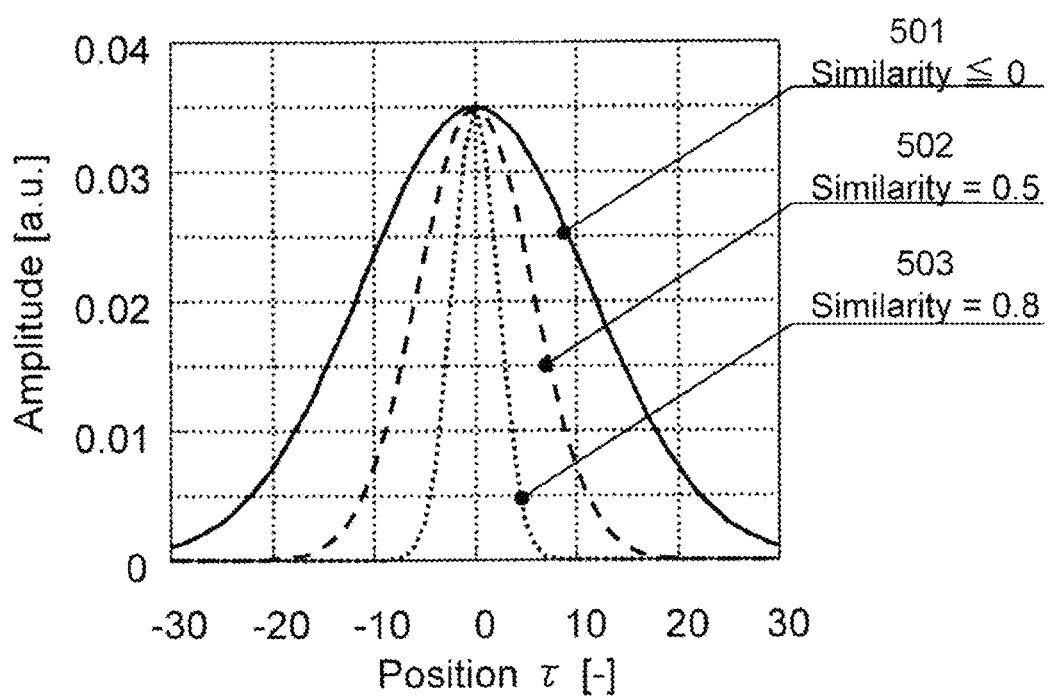
FIG. 9 is a graph showing the weighting function changes of the filters based on the similarities in the first embodiment.

FIG. 9 is an example of generating a weighting function $h_{Denoise}(\tau)$ according to the formula (9). The solid line 501 shows the weighting function in a case where a similarity is equal to or less than 0, the dashed line 502 shows the weighting function in a case where a similarity is 0.5, and the dotted line 503 shows the weighting function in a case where a similarity is 0.8. As shown in the present diagram, the weighting function has a steeper shape as a similarity is higher. By performing a smoothing process using such weighting functions, a pixel with a high similarity is hardly smoothed, and on the contrary to this, a pixel with a low similarity is greatly smoothed.

The denoising section 340 uses the calculated weighting function to perform a filtering process (smoothing) in the x direction (Step S1406).

Next, the denoising section 340 performs the similar process in the y direction. That is, the processes from the following Steps S1409 to S1411 are repeated for each pixel p (Steps S1408 and S1412). First, the similarity map Similarity Y(m, n, x, y) in the y direction of the pixel p=(x, y) is loaded (Step S1409). Then, a weighting function is generated using the loaded similarity map Similarity Y(m, n, x, y) (Step S1410). The weighting function is generated according to the above formula (9), for example. Then, the generated weighting function is used for performing a filtering process (smoothing) in the y direction (Step S1411).

Then, the denoising section 340 stores an acquired image as the denoised image deN(m, n) 450 in the storage device 172 (Step S1413).

<Image Synthesizing Process>

Figure 10:
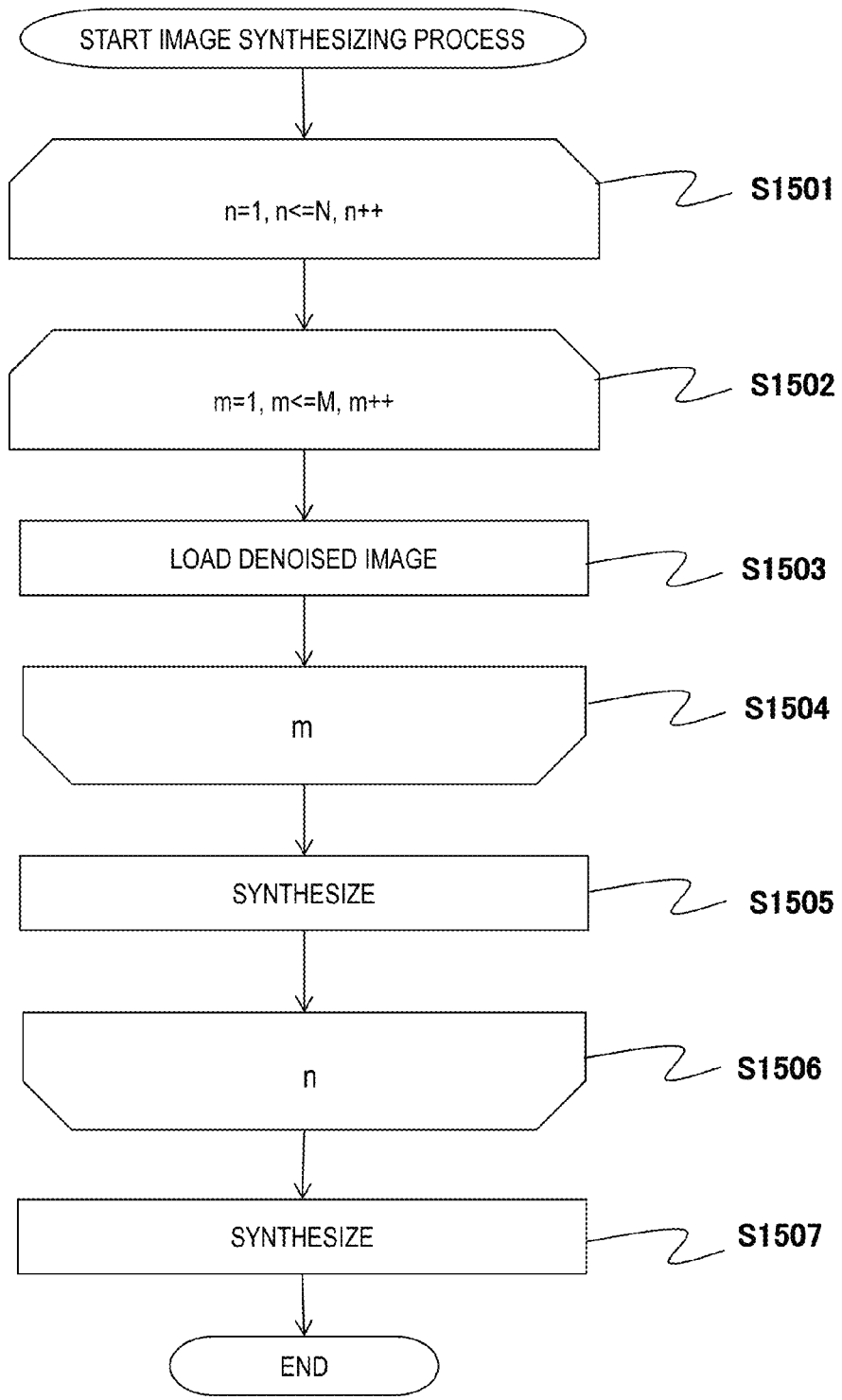
FIG. 10 is a flow chart of the image synthesizing process of the first embodiment.

Next, the image synthesizing process by the synthesizing section 350 will be described. FIG. 10 is a flow of the image synthesizing process of the present embodiment. Here, the denoised images deN(m, n) 450 generated from the same original image 410 are synthesized to acquire denoised images (synthesized denoised images) deNaI(n) in all the N wavelength bands. Then, all the synthesized denoised images deNaI(n) are synthesized to eventually acquire the one synthesized image 460.

Therefore, the synthesizing section 350 executes the processes from Steps S1502 to S1505 for the respective original images 410 that are the originals of the denoised images deN(m, n) 450 (Steps S1501 and S1506).

The synthesizing section 350 loads and synthesizes all the denoised images deN(m, n) 450 of the wavelength-band original images 420 generated from the same original image 410 (Steps S1502, S1503, and S1504) to generate denoised images deNaI(n) in all the wavelength bands (Step S1505). In the present embodiment, deN(1, n) and deN(2, n) are loaded and synthesized to generate a synthesized denoised image deNaI(n).

When all the synthesized denoised images are generated, the synthesizing section 350 synthesizes all the synthesized denoised images that were acquired to acquire the synthesized image 460 (Step S1507).

Additionally, simple addition or calculation such as obtaining a square root of the sum of the squares in a case where an image group was acquired by a plurality of the reception coils 161, for example, may be used for the synthesization to be executed by the synthesizing section 350.

Here, an image acquired by simply adding the original image group 410 acquired using a plurality of the reception coils 161 is compared with an image (the synthesized image 460) acquired by performing the filtering process of the present embodiment for the said original image group 410. In FIG. 11(a), the profile 601 of the image acquired by the simple addition and the profile 602 of the image (the synthesized image 460) acquired by the filtering process of the present embodiment are shown. In the present diagram, the thin line is the profile 601, and the thick line is the profile 602. Also, the diagram enlarging the dot and dash line portion 603 of FIG. 11(a) is shown in FIG. 11(b). As shown in these diagrams, the profile 602 of the image (the synthesized image 460) acquired by the filtering process of the present embodiment keeps the structure while reducing noise compared to the profile 601 of the image acquired by simply adding the original images.

Finally, the GUI (Graphical User Interface) of the present embodiment will be described. A variable that should be specified by an operator to execute the filter process of the present embodiment is a maximum noise wavelength $\lambda_{Noise}$ determining a cut-off wavelength to be used by the band dividing section 310.

Figure 12:
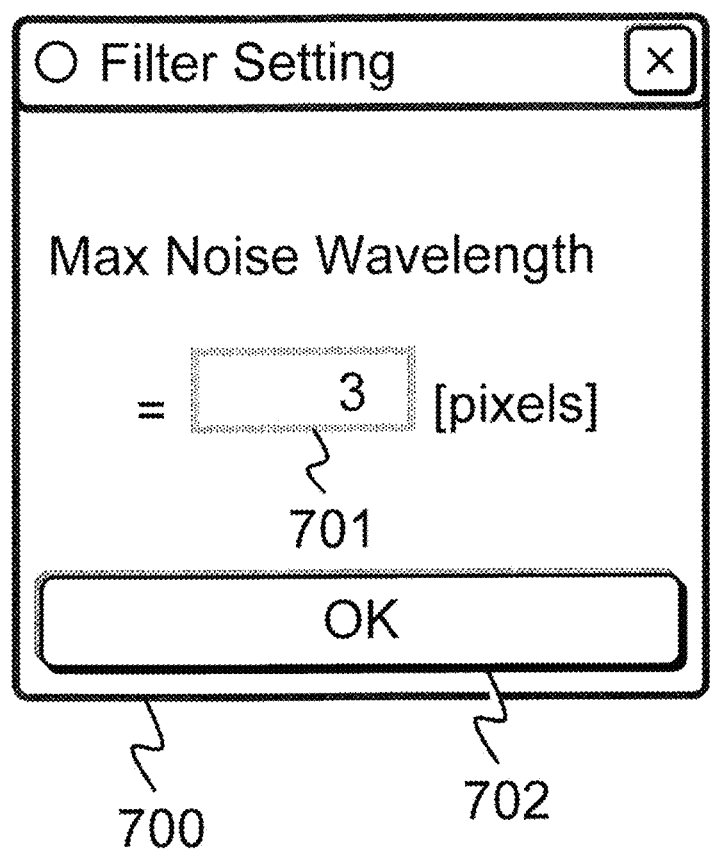
FIG. 12 is a diagram for explaining an example of the GUI of the first embodiment.

An example of the GUI 700 of the present embodiment is shown in FIG. 12. As shown in the present diagram, the GUI 700 of the present embodiment comprises the box 701 receiving a maximum noise wavelength $\lambda_{Noise}$ and the button 702 receiving a determining intention and functions as a setting receiving unit receiving the setting for the maximum noise wavelength $\lambda_{Noise}$. The band dividing section 310 receives the maximum noise wavelength $\lambda_{Noise}$ through the GUI 700.

The GUI 700 is displayed on the display device 173 and operated through the input device 174. An operator inputs a maximum noise wavelength to the box 701 and presses the button 702 to complete the setting. When the band dividing section 310 receives the button 702 being pressed down, the band dividing section 310 receives a value input in the box 701 then as a maximum noise wavelength $\lambda_{Noise}$.

Although a maximum noise wavelength $\lambda_{Noise}$ to be set may be normally 3 [pixels] as described above, the value is increased proportionally to an interpolation magnification in case of an interpolated image. Moreover, the maximum noise wavelength $\lambda_{Noise}$ is a variable for adjusting the degree of smoothing by a filter process. Therefore, a large numerical value is input in case of increasing the degree of smoothing, and a small numerical value is input in case of reducing the degree of smoothing. Since signal components equal to or less than the input maximum noise wavelength are removed, an operator should set a value according to the resolution to be calculated for a processed image.

Additionally, the GUI 700 is designed so that an operator sets a maximum noise wavelength.

Therefore, the configuration is not limited to the above. Without necessarily using a text box, it may be configured so that the other input methods such as a slider bar are feasible.

As described above, the image processing unit 230 of the present embodiment comprises the band dividing section 310 for dividing a plurality of the original images 410 in each predetermined wavelength band and generating a plurality of the wavelength-band original images 420, the reference image generating section 320 for synthesizing the plurality of the wavelength-band original images 420 in the respective wavelength bands to generate the reference images 430 in the respective wavelength bands, the similarity calculating section 330 for comparing the plurality of the wavelength-band original images 420 with the reference images 430 in the same wavelength band respectively to calculate the similarity map 440 for the respective wavelength-band original images 420, the denoising section 340 for generating the denoised images 450 respectively from the wavelength-band original images 420 by smoothing the plurality of the wavelength-band original images 420 respectively using the similarity map 440 of the said wavelength-band original images 420, and the synthesizing section 350 for synthesizing the denoised images 450 to generate the synthesized image 460.

For example, pixel value fluctuation by noise is recognized and saved as a texture and structure because a single image is used for processing in a method, such as described in the non-patent literature 1 etc., where the structure such as a directionality and an edge of a target pixel and the surrounding textures is detected to change a filter shape. However, in the method of the present embodiment, the reference image 430 is generated by synthesizing a plurality of images in which different random noises are superimposed (the wavelength-band original image group 420). Then, a similarity (the similarity map 440) calculated by comparing the acquired reference image 430 with the respective images (the wavelength-band original image group 420) is set as an index of the structure. Therefore, an error recognizing random noises as a structure can be reduced.

Additionally, according to the present embodiment, the original image group 410 is divided in a wavelength band to be determined from a maximum noise wavelength. Therefore, influence of data in a wavelength band different from the noise wavelength band hardly appears on the calculated similarity. Hence, a noise detection ability is increased.

Also, because smoothing is performed by selecting only data close to a pixel value of a target pixel when a pixel value difference between the target pixel and the surroundings is reflected on weighting, an image after filtering tends to be flat. However, in the method of the present embodiment, denoising or filtering is performed based on a similarity of the reference image 430. Hence, because a proactive assumption (that a structure can be saved when smoothing is performed using data of the same pixel value level) is not required, artificial process results are hardly caused. Additionally, because a denoising process is performed based on the calculated similarity, a directionality and an edge of a texture do not need to be assumed. Therefore, satisfactory denoising process results can be obtained in images of various shapes.

Additionally, the filter process of the present embodiment does not need a complex variable setting. Because an operator should set only a single variable (maximum noise wavelength), the process results can be easily imagined, which can achieve easy operation.

As described above, according to the present embodiment, errors in assessment of a structure caused by noise are reduced, and the noise superimposed in an image can be removed without causing artificiality in the result image after the removal while retaining significant information.

Additionally, in the present embodiment, a band dividing process may not be performed. In this case, the band dividing section 310 may not be provided.

Even in such a configuration, according to the present embodiment, the reference image 430 generated from the original image group 410 is compared with the original image group 410 to calculate a similarity, and the calculated similarity is set as an index of noise determination. Therefore, errors in assessment that recognize noise superimposed in an image as a significant signal are reduced. Also, because a denoising process is performed using the calculated similarity, a directionality and an edge of a texture do not need to be assumed. Therefore, satisfactory denoising process results can be obtained in images of various shapes.

Additionally, although a case where the CPU 171 of the MRI apparatus 100 achieves the above image processing unit 230 is described as an example in the present embodiment, this is not the only case. The functions of the image processing unit 230 may be built on the other information processing device that can transmit/receive data to/from the MRI apparatus 100.

Also, although a case of using the MRI apparatus as an apparatus acquiring original images to be processed by the image processing unit 230 is described as an example in the present embodiment, an image acquiring apparatus is not limited to this. The other medical image acquiring apparatus may be used. For example, an image group in which the same target is repeatedly measured by an ultrasonic diagnosis apparatus or a CT (Computed Tomography) apparatus can be used as an original image group to perform the same process. Additionally, the original images may not be medical images acquired by the medical image acquiring apparatus.

Second Embodiment

Next, the second embodiment to which the present invention is applied will be described. In the present embodiment, a flexible and adequate noise removal effect is obtained by repeating the filtering process of the first embodiment.

The configuration of the MRI apparatus 100 of the present embodiment is basically similar to the first embodiment. However, because the above process is performed repeatedly, the functions of the image processing unit 230 of the present embodiment are different. Hereinafter, the configuration different from the first embodiment will be mainly described in the present embodiment.

Figure 13:
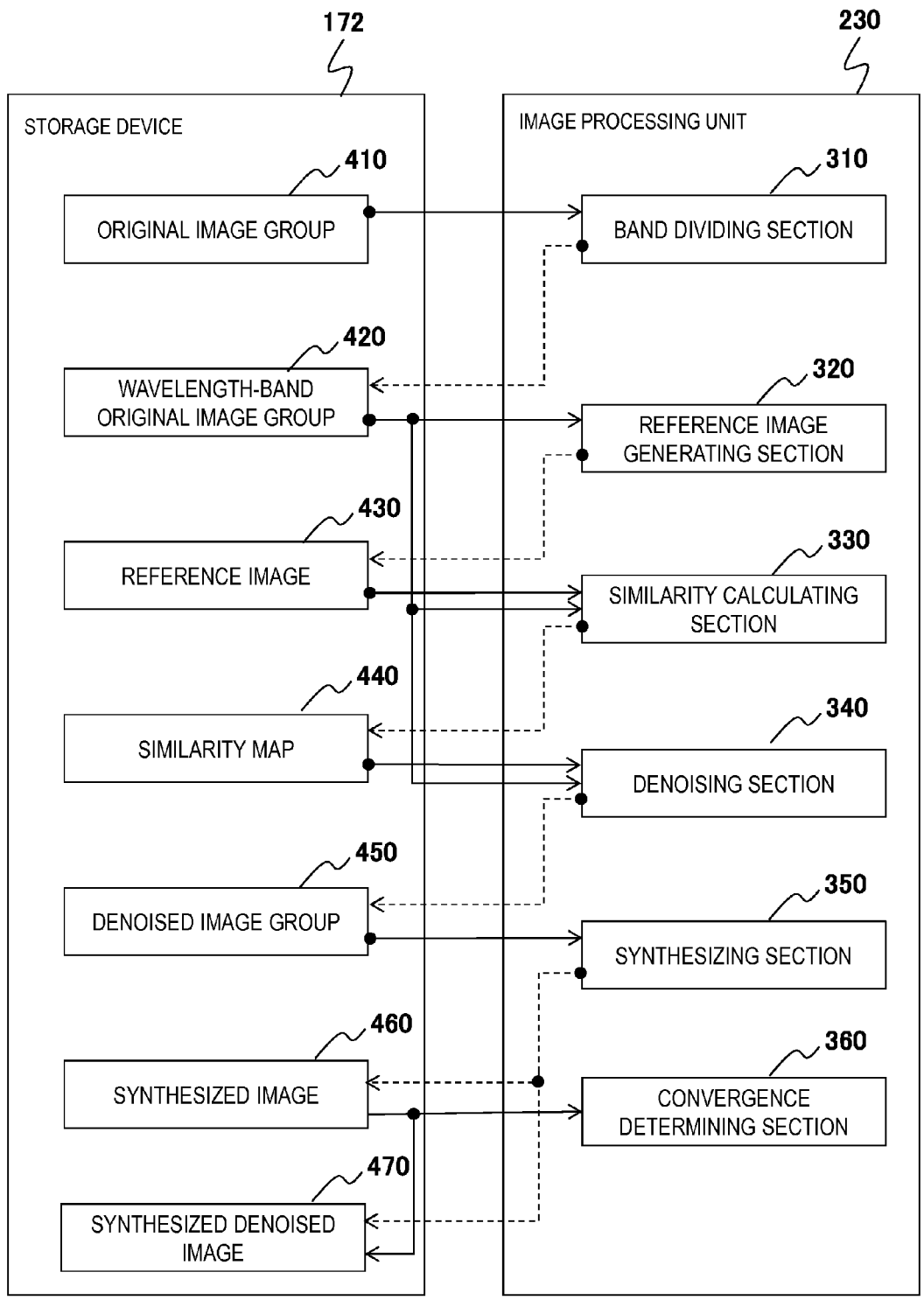
FIG. 13 is a diagram for explaining the functional blocks of the image processing unit of the second embodiment and data to be generated by each function.

In addition to the configuration of the first embodiment, the image processing unit 230 of the present embodiment determines whether or not the synthesized image 460 converges each time it is generated as shown in FIG. 13 and comprises the convergence determining section 360 replacing the original images 410 with synthesized denoised images generated just before in case of a negative determination.

The convergence determining section 360 determines whether or not the synthesized image 460 converges at a variation from the synthesized image 460 acquired in the last repetition. Here, it is determined that the convergence was made when the variation becomes less than a predetermined amount. For example, in a case where the following formula (10) is satisfied between the synthesized image $I_{Comp}$(RepeatNum, x, y) acquired in the RepeatNum-th time and the synthesized image $I_{Comp}$(RepeatNum−1, x, y) acquired in the (RepeatNum−1)-th time, it is determined that the convergence was made.

[Formula 10]

$$I \geq \frac{\sum_{i=1}^{X}\sum_{j=1}^{Y} \text{Abs}\{I_{Comp}(RepeatNum, i, j) - I_{Comp}(RepeatNum-1, i, j)\}}{\sum_{i=1}^{X}\sum_{j=1}^{Y} I_{Comp}(RepeatNum, i, j)} \times 100 \quad (10)$$

Here, X is the number of images in the x direction, Y is the number of images in the y direction, Abs is the absolute function, and RepeatNum is the number of repetition times. The formula (10) shows that a variation by the repetition process is equal to or less than 1% to the pixel value total of an entire image. Additionally, the convergence criterion is not limited to this.

It may be configured so that a user can set a maximum variation value to determine a convergence.

Additionally, the convergence determining section 360 cannot calculate the above formula (10) for the synthesized image $I_{Comp}$(1, x, y) acquired in the first time and always determines that the convergence is not made.

Figure 14:
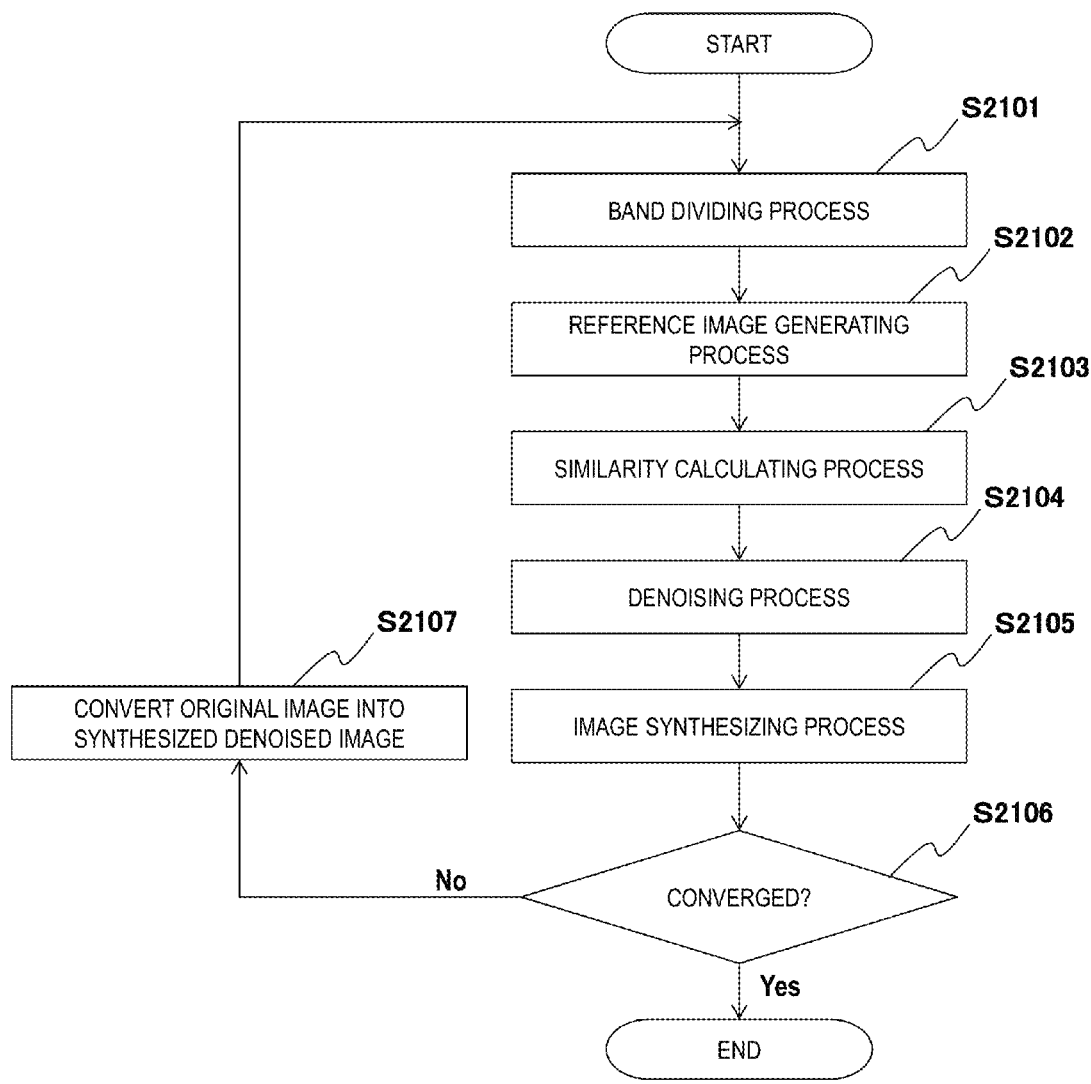
FIG. 14 is a flow chart of the filtering process of the second embodiment.

Hereinafter, the flow of the filtering process by the image processing unit 230 of the present embodiment will be described. FIG. 14 is a process flow for explaining the filtering process of the present embodiment.

Similarly to the first embodiment, the band dividing section 310 performs a band dividing process (Step S2101), the reference image generating section 320 performs a reference image generating process (Step S2102), the similarity calculating section 330 performs a similarity calculating process (Step S2103), the denoising section 340 performs a denoising process (Step S2104), and then the synthesizing section 350 performs a synthesizing process (Step S2105). However, in the present embodiment, the synthesizing section 350 also stores the synthesized denoised images 470 in the storage device 172.

When acquiring the synthesized image 460, the convergence determining section 360, for example, calculates the above formula (10) and determines whether or not the acquired synthesized image 460 converges (Step S2106). When it is determined that the convergence was made, the process ends. On the other hand, when it is determined that the convergence was not made, the convergence determining section 360 replaces the original image group 410 with the synthesized denoised image group 470 calculated just before (Step S2107), and then the procedure goes back to Step S2101. Additionally, the image conversion should be performed after generating synthesized denoised images and may be performed before the convergence determination.

As described above, according to the present embodiment, similarly to the first embodiment, the reference image 430 is generated by synthesizing a plurality of the original images 410, a similarity is calculated by comparing the generated reference image 430 with the plurality of the original images 410 respectively, and then the calculated similarity is set as an index of noise determination to perform a denoising process. At this time, the reference image generation, the similarity calculation, and the denoising process may be performed for each predetermined wavelength band. Therefore, similarly to the first embodiment, errors in assessment that recognize noise superimposed in an image as a significant signal are reduced. Also, because a denoising process is performed using the calculated similarity, a directionality and an edge of a texture do not need to be assumed. Therefore, satisfactory denoising process results can be obtained in images of various shapes.

Additionally, an image after denoising is set as an original image, the denoising process is repeated until the image converges, and there is no need to adjust a denoising effect (degree of smoothing) of the denoising process. Therefore, the present embodiment can be applied to various images without adjusting a processing parameter.

Additionally, in the present embodiment, similarly to the first embodiment, an apparatus acquiring the original images 410 to be processed by the image processing unit 230 is not limited to an MRI apparatus. The other medical image acquiring apparatus may be used. Also, except the medical image acquiring apparatus, an apparatus that can acquire images may be used.

Third Embodiment

Next, the third embodiment to which the present invention is applied will be described. In the present embodiment, the filtering process is repeated while changing a cut-off wavelength to be used for a band dividing process.

The configuration of the MRI apparatus of the present embodiment is basically similar to the first embodiment.

However, because the above process is performed repeatedly, the functions of the image processing unit 230 of the present embodiment are different. Hereinafter, the configuration different from the first embodiment will be mainly described in the present embodiment.

Figure 15:
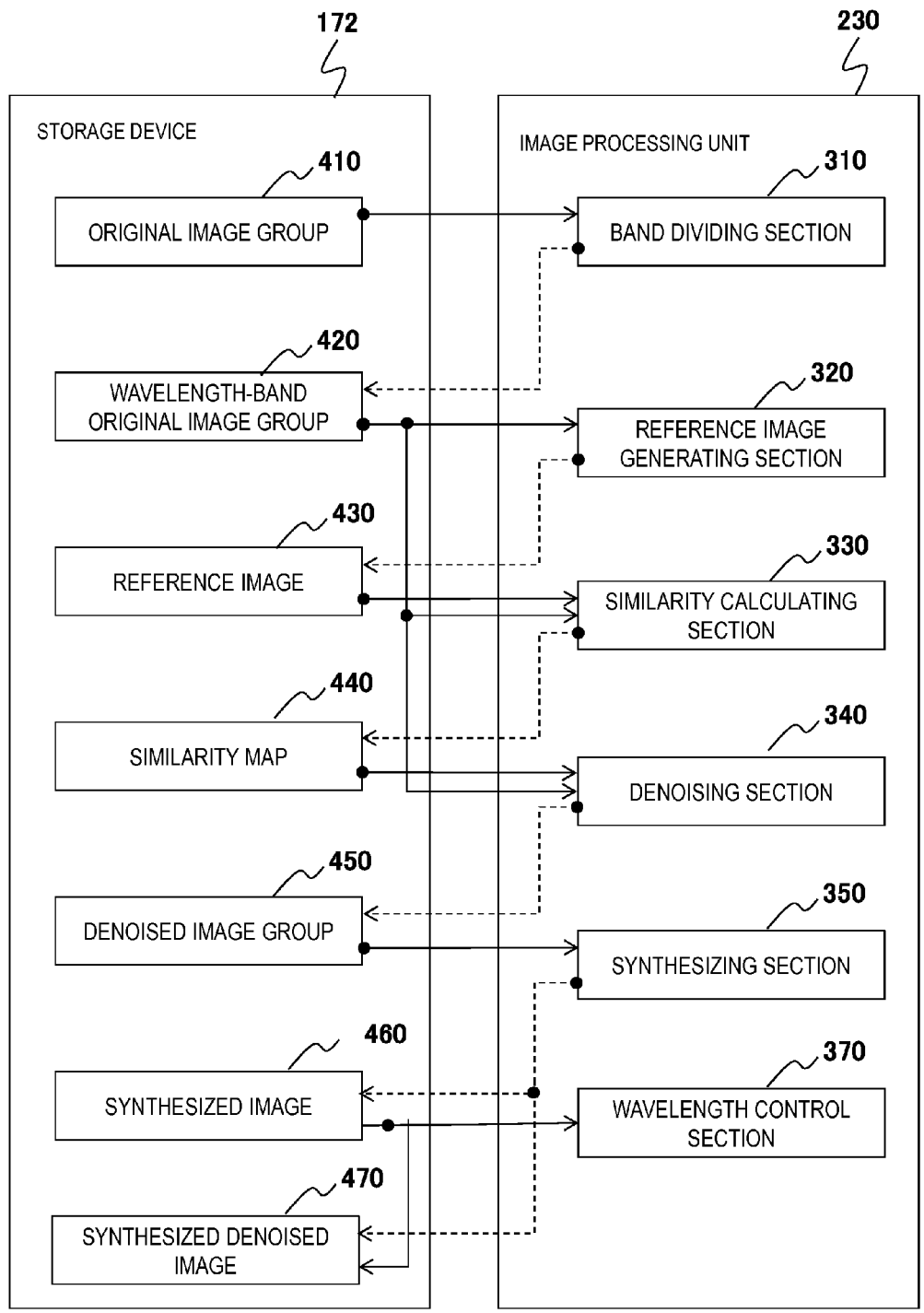
FIG. 15 is a diagram for explaining the functional blocks of the image processing unit of the third embodiment and data to be generated by each function.

The image processing unit 230 of the present embodiment comprises the wavelength control section 370 as shown in FIG. 15 in addition to the configuration of the first embodiment. Also, in the present embodiment, the band dividing section 310 uses 1 cut-off wavelength to divide the original images 410 into two of the wavelength-band original images 420. Then, a denoising process is performed only for the wavelength-band original image 420 with a smaller wavelength band.

The wavelength control section 370 of the present embodiment repeats increasing and updating the cut-off wavelength set at the minimum value in the predetermined wavelength band by a predetermined increment as well as replaces the original images 410.

Since thermal noise included in an NMR signal has an almost uniform amplitude spectrum in all the wavelength band, the noise wavelength band is from 0 to infinity. However, noise that should be removed particularly in MRI is short-wavelength noise making a fine structure less visible. Therefore, it is practical and desirable that a wavelength band changing a cut-off wavelength is set to approximately 3 to 12 [pixels]. Additionally, it is desirable that a broader wavelength band is set when an image is interpolated at a high magnification.

It may be configured so that an operator sets the wavelength band changing a cut-off wavelength, or it may be configured so that the wavelength band is predetermined and stored in the storage device 172. Also, an increment for changing may be configured similarly.

Figure 16:
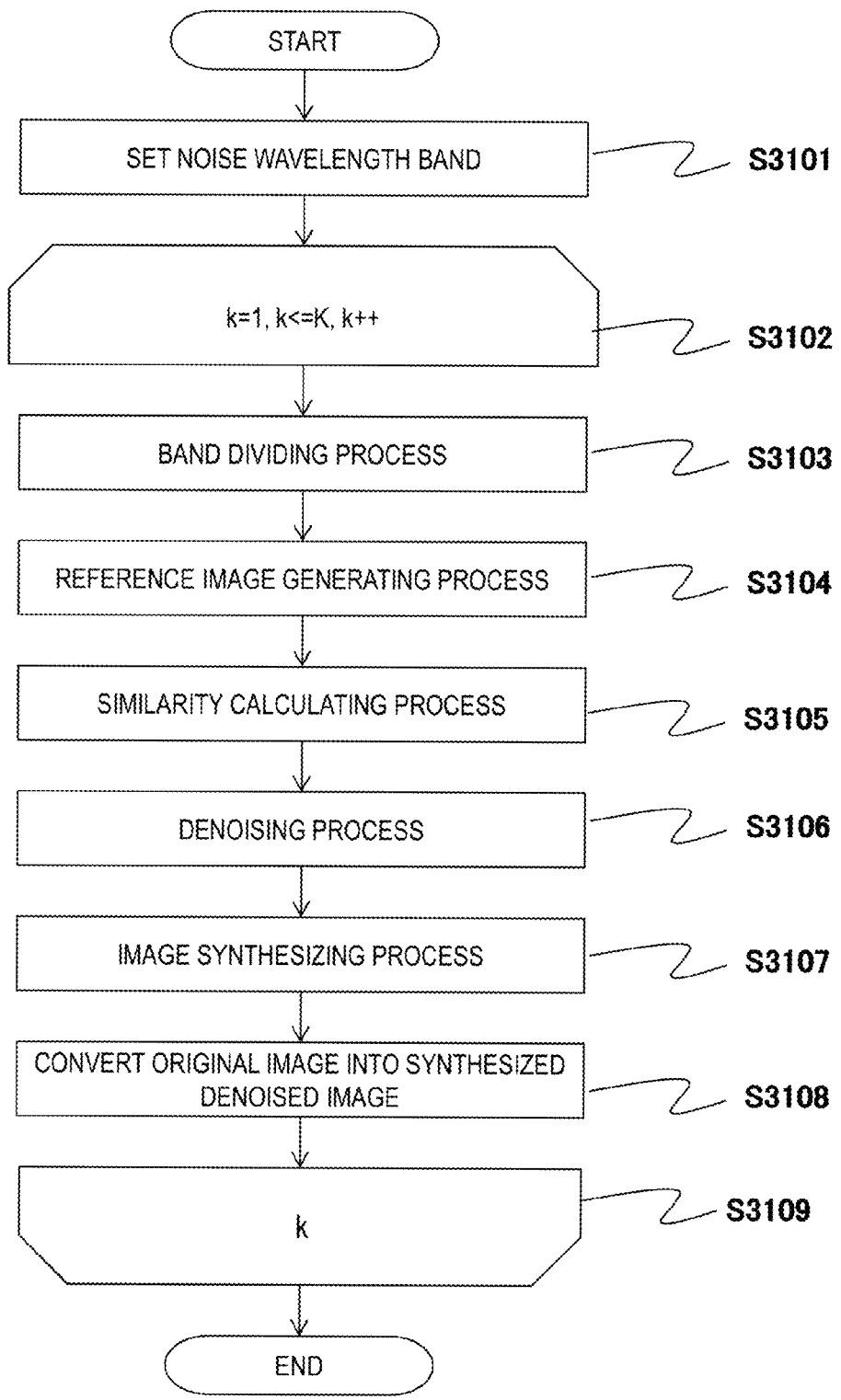
FIG. 16 is a flow chart of the filtering process of the third embodiment.

Hereinafter, a filtering process flow of the image processing unit 230 of the present embodiment will be described. FIG. 16 shows a process flow for explaining the filtering process flow of the present embodiment.

First, the wavelength control section 370 sets a wavelength band of noise as a range to change a cut-off wavelength (Step S3101). The setting range is as described above. At the same time, an increment is also set to calculate a loop counter k and the maximum value K of k. For example, the minimum value of the wavelength band of noise is set as $\lambda_{min}$, the maximum value is set as $\lambda_{max}$, and the increment is set as $\Delta\lambda$. A cut-off wavelength $\lambda_{cutoff}$ is calculated in $\lambda_{cutoff}=\lambda_{min}+\Delta\lambda(k-1)$ using the loop counter k. Also, the maximum value K of the counter k is calculated in K=Int$((\lambda_{max}-\lambda_{min})/\Delta\lambda)$. Additionally, Int(x) is a function to return an integer of the value x. Moreover, a cut-off wavelength is expressed as $\lambda_{cutoff}(k)$ in a case where a counter is k.

For example, as described above, in case of setting 3 to 12 [pixels] as a wavelength band of noise and 1 pixel as an increment $\Delta\lambda$, K becomes 10.

The wavelength control section 370 changes the loop counter k from 1 to K by 1 increment to repeat the processes from Steps S3103 to S3108 (Steps S3102 and S3109).

The band dividing section 310 uses a cut-off wavelength $\lambda_{cutoff}(k)$ to perform a band dividing process for the respective original images 410 (Step S3103). Here, the respective original images 410 are divided into two wavelength bands using the cut-off wavelength $\lambda_{cutoff}(k)$. Then, the wavelength-band original images 420 in a wavelength band equal to or less than the cut-off wavelength $\lambda_{cutoff}(k)$ are set as the first wavelength-band original images $I_{Sep}(1, n, x, y)$, and those in the other wavelength band are set as the second wavelength-band original images $I_{Sep}(2, n, x, y)$.

Next, the reference image generating section 320 performs a reference image generating process (Step S3104). In the present embodiment, because a denoising process is performed only for the first wavelength-band original images $I_{Sep}(1, n, x, y)$ that are the wavelength-band original images 420 equal to or less than the cut-off wavelength $\lambda_{cutoff}(k)$, the reference images 430 are also generated only from the first wavelength-band original image $I_{Sep}(1, n, x, y)$. That is, the reference image generating section 320 of the present embodiment loads and synthesizes all the first wavelength-band original images $I_{Sep}(1, n, x, y)$ to generate the first reference image $I_{Ref}(1, x, y)$.

Next, the similarity calculating section 330 performs a similarity calculating process (Step S3105). In the present embodiment, similarities in the x and y directions are calculated for each pixel of the first wavelength-band original image $I_{Sep}(1, n, x, y)$ using the first reference image $I_{Ref}(1, x, y)$ to generate a similarity map of the first wavelength-band original image $I_{Sep}(1, n, x, y)$.

The denoising section 340 performs a denoising process for the first wavelength-band original image $I_{Sep}(1, n, x, y)$ (Step S3106). Also in the denoising process, the process is performed only for each pixel of the first wavelength-band original image $I_{Sep}(1, n, x, y)$ to generate a denoised image of the first wavelength-band original image $I_{Sep}(1, n, x, y)$ (hereinafter, referred to as the first denoised image).

Next, the synthesizing section 350 performs an image synthesizing process (Step S3107). In the present embodiment, the first denoised image generated from the same original image 410 and the second wavelength-band original image $I_{Sep}(2, n, x, y)$ are synthesized to acquire the synthesized denoised image 470 of one of the original images. Then, all the synthesized denoised images are synthesized to acquire the synthesized image 460. In the present embodiment, the synthesizing section 350 also stores the synthesized denoised images in the storage device 172.

Next, the wavelength control section 370 replaces the original image group 410 with the acquired synthesized denoised image group 470 (Step S3108).

Additionally, it may be configured so that the synthesized denoised images 470 are synthesized to acquire the synthesized image 460 after only the synthesized denoised images 470 are calculated and all of the loop processes end in Step S3107 during the above loop process.

As described above, according to the present embodiment, similarly to the first embodiment, a similarity is calculated by comparing the reference image 430 generated from a plurality of the original images 410 with the original image 410, and then the calculated similarity is set as an index of noise determination to perform a denoising process. Therefore, the effect similar to the first embodiment can be obtained.

Additionally, according to the present embodiment, because the above processes are repeated while a cut-off wavelength is being increased in a predetermined wavelength band of noise, strict definition of the maximum noise wavelength is not required. Therefore, noise can be removed accurately without setting a strict processing parameter.

Additionally, also in the present embodiment, similarly to the first embodiment, an apparatus acquiring the original images 410 to be processed by the image processing unit 230 is not limited to an MRI apparatus. The other medical image acquiring apparatus may be used. Also, except the medical image acquiring apparatus, an apparatus that can acquire images may be used.

Figure 17:
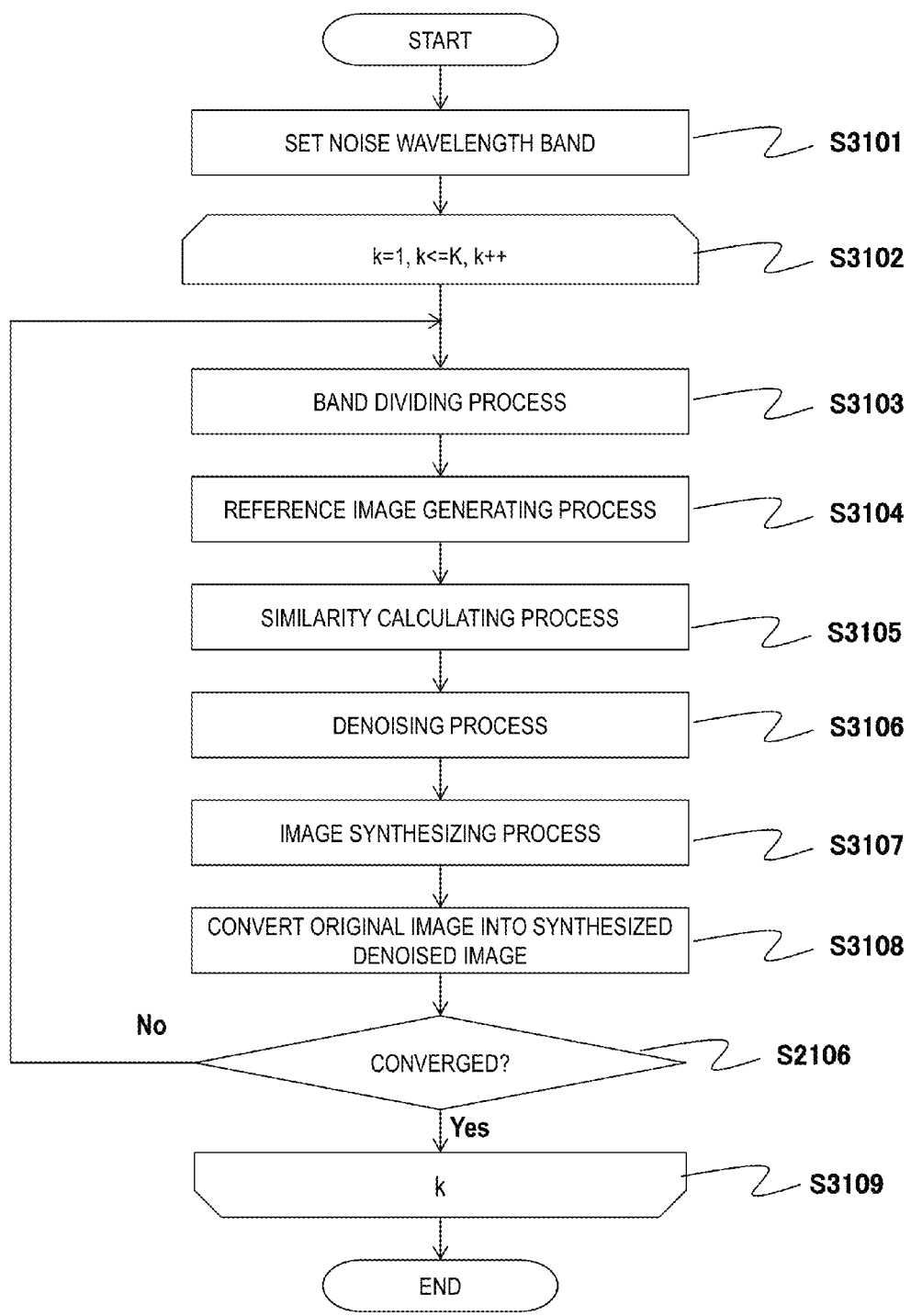
FIG. 17 is a flow chart of the filtering process in which the second and third embodiments are combined.

Also, the loop process of the present embodiment may be combined with the convergence determining process of the second embodiment. In this case, whether or not the synthesized image 460 converges each time it is generated is determined, and the convergence determining section 360 replacing the original images 410 with the synthesized denoised images 470 is further comprised in case of a negative determination. A process flow in this case is shown in FIG. 17.

As shown in the present diagram, the processes from Steps S3103 to S3108 of the present embodiment are performed for each cut-off wavelength, and then the convergence determining process of the second embodiment (Step S2106) is performed. In case of a negative determination in the convergence determining process, the processes from Step S3103 are repeated again. Then, after determining that the convergence was made in the convergence determining process, a cut-off wavelength is updated (Steps S3102 and S3109).

Fourth Embodiment

Next, the fourth embodiment to which the present invention is applied will be described. In the first and second embodiments, a plurality of original images are acquired in advance to perform the above image processing. However, in the present embodiment, data that can generate one image using an MRI apparatus is acquired, and then a plurality of original images are generated from the data.

The MRI apparatus 100 of the present embodiment is basically similar to that of the first embodiment. However, in the present embodiment, a plurality of original images are generated from the acquired data for one image. Hence, the image reconstruction unit 220 generates a plurality of original images from one image. Hereinafter, the configuration different from the first embodiment will be mainly described in the present embodiment.

As shown in FIG. 2, the image reconstruction unit 220 of the present embodiment comprises the missing data generating section 221 for generating a plurality of missing raw data whose missing regions are respectively different from one of raw data acquired by the imaging unit 210, the estimated data generating section 222 for generating estimated data from each of the missing raw data, and the original image generating section 223 for reconstructing original images respectively from each of the estimated data.

Hereinafter, a generating process of the original image group 410 by each part of the image reconstruction unit 220 of the present embodiment will be described using FIG. 18. The raw data 801 is acquired by the imaging unit 210, in which NMR signals for one image are arranged in the k-space.

The missing data generating section 221 generates a plurality of the missing raw data 802 from the acquired raw data 801. The missing raw data 802 is that in which data in a partial region is zeroed out in the k-space where the raw data 801 is arranged. At this time, missing regions are changed respectively to generate a plurality of the missing raw data 802.

A missing region is equal to or less than the half of all the raw data. Also, it is desirable so that the region is not missing the central portion.

The estimated data generating section 222 uses a publicly known k-space estimation technique, a region where the missing raw data group 802 is zeroed out respective is filled with data, and then the estimated raw data group 803 is generated. Additionally, in the k-space estimation technique, a technique is used to fill a missing region with data of a non-missing region described in the non-patent literature 2, for example.

The original image generating section 223 generates the original image group 804 by performing the Fourier transform for each of the estimated raw data group 803 to reconstruct images.

Figure 18:
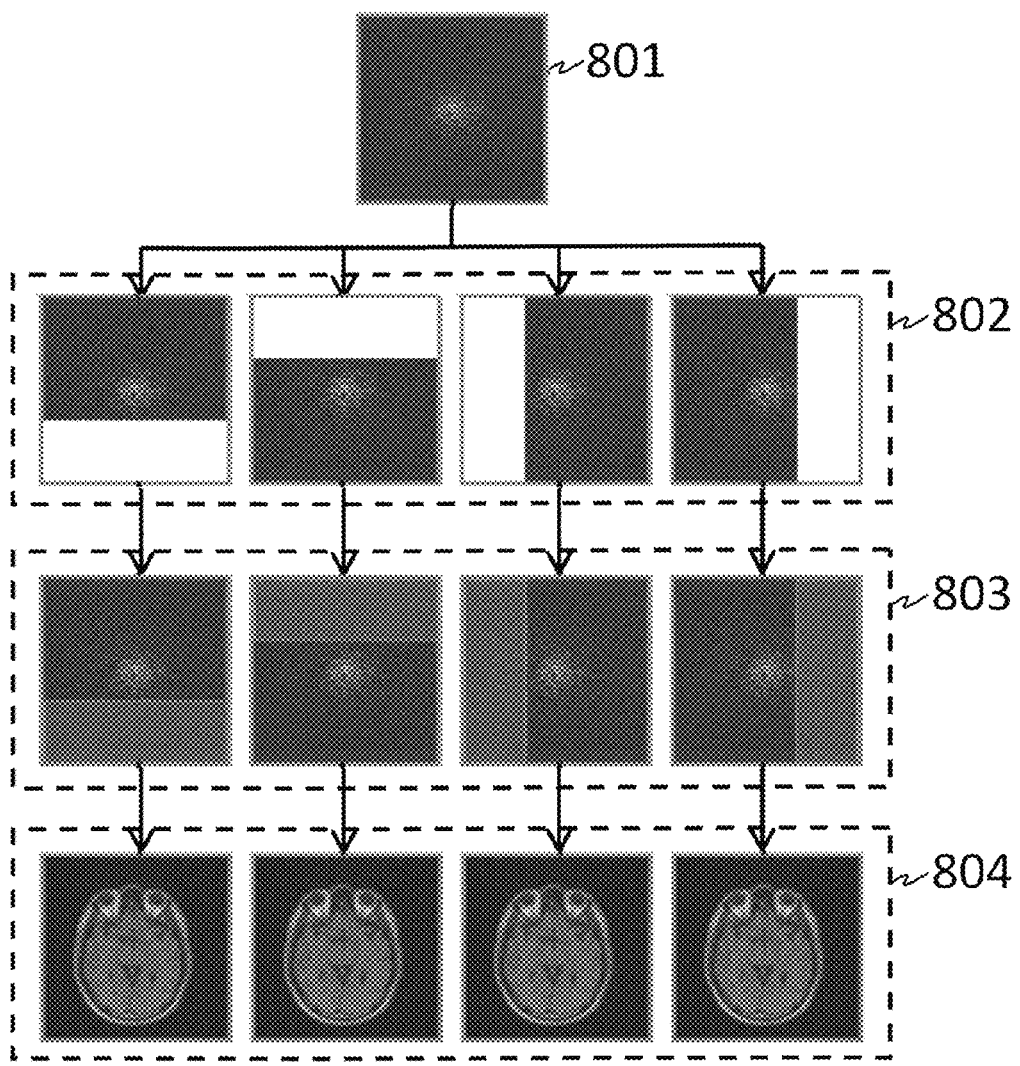
FIG. 18 is a diagram for explaining a generation process of original image groups in the fourth embodiment.

Although the original image group 804 of the present embodiment is generated from the raw data 801 of one image the as shown in FIG. 18, noise in different regions on the k-space is emphasized because different missing regions are respectively estimated, which results in having different noise. Because the respective original images 804 have different noise, the noise and significant signals can be distinguished by comparing with a reference image to be generated from the original image group 804.

The subsequent processes using the generated the original images 804 are similar to any of the first, second, and third embodiments.

As described above, according to the present embodiment, the effect similar to each embodiment above can be obtained in the filtering process by the image processing unit 230. Additionally, in the present embodiment, the original image group 410 can be obtained by the single reception coil 161 or in one measurement.

Additionally, although a Gaussian filter described in the formulas (4) and (5) is used for wavelength band division in each embodiment above for example, the filter is not limited to the Gaussian filter. For example, a spline filter and an arbitrary filter with amplitude transmission characteristics can be used.

Also, although similarity calculation is performed using the formulas (7) and (8) in each embodiment above, the similarity calculation is not limited to this. For example, a square sum of the deviation between a reference image and a wavelength-band division image may be used.

Also, although a weighting function $h_{Denoise}(\tau)$ to be used for filtering is calculated according to the formula (9) in a denoising process in each embodiment above, the weighting function is not limited to this. For example, an outlier process by a median filter or by comparing images may be performed.

Also, original images to be processed in each embodiment above are not limited to two-dimensional images, but may be three-dimensional images. Also, a smoothing degree may be changed according to the dimension. The smoothing degree can be changed by changing the settings for the maximum noise wavelength. Additionally, in order to specify the smoothing degree, the definition of the maximum noise wavelength may not be used. For example, the smoothing degree may be adjusted such as by multiplying the Similarity X and Similarity Y calculated in a similarity calculating process by a coefficient.

DESCRIPTION OF REFERENCE NUMERALS

100: MRI apparatus, 101: object, 120: static magnetic field generation system, 130: gradient magnetic field generation system, 131: gradient magnetic field coil, 132: gradient magnetic field power source, 140: sequencer, 150: high-frequency magnetic field generation system (transmission system), 151: transmission coil, 152: high-frequency oscillator, 153: modulator, 154: high-frequency amplifier, 160: high-frequency magnetic field detection system (reception system), 161: reception coil, 162: signal amplifier, 163: quadrature phase detector, 164: A/D converter, 170: control processing system, 171: CPU, 172: storage device, 173: display device, 174: input device, 210: imaging unit, 220: image reconstruction unit, 221: missing data generating section, 222: estimated data generating section, 223: original image generating section, 230: image processing unit, 310: band dividing section, 320: reference image generating section, 330: similarity calculating section, 340: denoising section, 350: synthesizing section, 360: convergence determining section, 370: wavelength control section, 410: original image, 420: wavelength-band original image, 430: reference image, 440: similarity map, 450: denoised image, 460: synthesized image, 470: synthesized denoised image, 501: solid line, 502: dashed line, 503: dotted line, 601: profile, 602: profile, 603: dot and dash line portion, 700: GUI, 701: box, 702: button, 801: raw data, 802: missing raw data, 803: estimated raw data, 804: original image

The invention claimed is:

1. An image processing device comprising:
an image processing unit for synthesizing a plurality of original images to generate a reference image, calculating a similarity for each of the plurality of original images by comparing with the generated reference image, smoothing the plurality of original images based on the calculated similarity, and synthesizing the plurality of smoothed original images to acquire a synthesized image
wherein the image processing unit comprises:
a band dividing section for dividing the plurality of original images for each predetermined wavelength band to generate a plurality of wavelength-band original images;
a reference image generating section for synthesizing the plurality of wavelength-band original images for each of the predetermined wavelength bands to generate the reference image for each of the wavelength bands;
a similarity calculating section for comparing each of the plurality of wavelength-band original images with the reference image in the same wavelength band to calculate the similarity for each of the wavelength-band original images;
a denoising section for generating denoised images from each of the wavelength-band original images by smoothing each of the plurality of wavelength-band original images using the similarity of the said wavelength-band original image; and
a synthesizing section for synthesizing the denoised images to generate the synthesized image.

2. The image processing device according to claim 1,
wherein the band dividing section calculates a cut-off wavelength from the from a predetermined maximum noise wavelength and generates the wavelength-band original images from each of the plurality of original images by the said cut-off wavelength.

3. The image processing device according to claim 1,
wherein the image processing unit determines whether or not the synthesized image converges each time it is generated and further comprises a convergence determining section for replacing the synthesized images with the original images in case of a negative determination,
the band dividing section divides the replaced original images each time the synthesized images are replaced with the original images to newly generate the wavelength-band original images,
the reference image generating section generates the reference image each time the wavelength-band original image is generated, and the similarity calculating section calculates the similarity each time the reference image is generated,
the denoising section generates the denoised image each time the similarity is calculated,
the synthesizing section synthesizes a denoised image generated from the same original image to generate a synthesized denoised image each time the denoised image is generated, and then synthesizes all the synthesized denoised images that were synthesized to generate the synthesized image, and
the convergence determining section replaces the original images with the synthesized denoised images generated just before in case of a negative determination.

4. The image processing device according to claim 2,
wherein the image processing unit repeats increasing and updating the cut-off wavelength set at the minimum value in the predetermined wavelength band by a predetermined increment and further comprises a wavelength control section for replacing the original images,
the band dividing section divides the replaced original images into two wavelength bands using the said cut-off wavelength each time the cut-off wavelength is set or updated and generates the first wavelength-band original image in a wavelength band equal to or less than the cut-off wavelength and the second wavelength-band original image in a wavelength band larger than the said cut-off wavelength,
the reference image generating section generates the reference image from the first wavelength-band original image each time the said first wavelength-band original image is generated,
the similarity calculating section calculates the similarity of the first wavelength-band original image each time the reference image is generated,
the denoising section generates the denoised image of the first wavelength-band original image each time the similarity is calculated,
the synthesizing section synthesizes the denoised image generated from the same original image and the second wavelength-band original image to generate a synthesized denoised image each time the denoised image is generated, and then synthesizes all the synthesized denoised images that were synthesized to generate the synthesized image, and
the wavelength control section replaces the original images with the synthesized denoised images generated just before when updating the cut-off wavelength.

5. The image processing device according to claim 4,
wherein the image processing unit determines whether or not the synthesized image converges each time it is generated and further comprises a convergence determining section for replacing the original images with the synthesized denoised images in case of a negative determination.

6. The image processing device according to claim 2,
wherein the image processing unit further comprises a setting receiving unit for receiving the setting for the maximum noise wavelength.

7. The image processing device according to claim 1,
wherein the similarity is a local similarity to the reference image for each pixel, and a weighting function to be calculated from the said similarity and used for the smoothing has a steeper shape as the said similarity is higher.

8. An image processing method comprising:

a band dividing process for dividing a plurality of original images respectively in each wavelength band to generate a plurality of wavelength-band original images;

a reference image generating process for synthesizing the plurality of wavelength-band original images in each of the wavelength bands to generate a reference image in each of the wavelength bands;

a similarity calculating process for comparing the plurality of wavelength-band original images respectively with the reference image in the same wavelength band to calculate a similarity for each of the wavelength-band original images;

a denoising process for smoothing the plurality of wavelength-band original images respectively based on the similarity of the said wavelength-band original image to generate a denoised image from each wavelength-band original image; and a synthesizing process for synthesizing the denoised images to generate a synthesized image.

9. The image processing method according to claim 8, further comprising:

a convergence determining process for determining whether or not the synthesized image converges each time it is generated, replacing the original images in case of a negative determination, and executing the band dividing process, the band dividing process, the reference image generating process, the similarity calculating process, the denoising process, and the synthesizing process until it is determined that the convergence was made, wherein the synthesizing process synthesizes a denoised image generated from the same original image each time the denoised image is generated to generate a synthesized denoised image, and then synthesizes all the synthesized denoised images that were generated to generate the synthesized image, and the convergence determining process replaces the original images with the synthesized denoised images.

* * * * *